US012702681B2

(12) United States Patent
Dai et al.

(10) Patent No.: US 12,702,681 B2
(45) **Date of Patent: *Aug. 11, 2026**

(54) **TUMOR IMMUNOTHERAPY COMPOSITION BASED ON ANTIGEN-PRESENTING CELLS ACTIVATED BY ATTENUATED *LISTERIA MONOCYTOGENES*, PREPARATION METHOD THEREFOR AND APPLICATION THEREOF**

(71) Applicants: Suzhou RoyalTech Med CO., Ltd, Suzhou (CN); Shanghai RoyalTech Med CO., Ltd, Shanghai (CN)

(72) Inventors: Nan Dai, Suzhou (CN); Yonggang Zhao, Suzhou (CN)

(73) Assignees: Suzhou RoyalTech Med CO., Ltd, Suzhou (CN); Shanghai Royaltech Med CO., Ltd, Pudong (CN)

(*) Notice: Subject to any disclaimer, the term of this patent is extended or adjusted under 35 U.S.C. 154(b) by 1399 days.

This patent is subject to a terminal disclaimer.

(21) Appl. No.: 17/265,314

(22) PCT Filed: Jul. 31, 2019

(86) PCT No.: PCT/CN2019/098594
§ 371 (c)(1),
(2) Date: Apr. 23, 2021

(87) PCT Pub. No.: WO2020/024982
PCT Pub. Date: Feb. 6, 2020

(65) Prior Publication Data

US 2021/0236545 A1 Aug. 5, 2021

(30) Foreign Application Priority Data

Aug. 2, 2018 (CN) ........................ 201810870350.1

(51) Int. Cl.
*A61K 35/15* (2025.01)
*A61K 39/00* (2006.01)
(Continued)

(52) U.S. Cl.
CPC .......... *A61K 35/15* (2013.01); *A61K 39/0208* (2013.01); *A61K 40/17* (2025.01);
(Continued)

(58) Field of Classification Search
CPC .... A61K 35/745; A61K 39/011; A61K 35/15; A61K 45/106; A61K 2039/5154;
(Continued)

(56) References Cited

U.S. PATENT DOCUMENTS 11,648,306 B2 * 5/2023 Dai .................... C07K 14/4748 424/190.1
2004/0197343 A1 * 10/2004 Dubensky, Jr. ......... A61P 37/08 424/184.1
(Continued)

FOREIGN PATENT DOCUMENTS

CN 102076843 A 5/2011
CN 107847611 3/2018
(Continued)

OTHER PUBLICATIONS

Wikipedia page; https://en.wikipedia.org/wiki/Listeriolysin_O. (Year: 2021).*
(Continued)

*Primary Examiner* — Samira J Jean-Louis
*Assistant Examiner* — Amelia Nicole Dickens
(74) *Attorney, Agent, or Firm* — Fish & Richardson P.C.

(57) ABSTRACT

A tumor immunotherapy composition based on modified cells, in particular antigen-presenting cells activated by means of attenuated *Listeria monocytogenes*, a preparation method therefor and an application thereof. Attenuated *List-*
(Continued)

eria monocytogenes carrying a specific antigen plasmid is used to activate antigen-presenting cells, thereby activating MHC antigen presenting properties and a series of cellular immune responses in vivo so as to achieve the purpose of anti-tumor therapy. The described technical solution may specifically activate macrophages and/or dendritic cells, thereby eliciting a series of specific anti-tumor immune responses. The operation process does not require genetic modification of autologous cells, is not limited by tumor type, and operations of the overall process are simple, easy-to-implement and reproducible. The tumor immunotherapy composition of the present disclosure may activate a series of anti-tumor immune responses in vivo, thereby greatly shortening the treatment process and significantly improving targeting ability and safety.

20 Claims, 16 Drawing Sheets

Specification includes a Sequence Listing.

(51) Int. Cl.

| | |
|---|---|
| ***A61K 39/02*** | (2006.01) |
| ***A61K 40/17*** | (2025.01) |
| ***A61K 40/19*** | (2025.01) |
| ***A61K 40/24*** | (2025.01) |
| ***A61K 40/42*** | (2025.01) |
| ***A61K 45/06*** | (2006.01) |
| ***A61P 35/00*** | (2006.01) |
| ***C12N 5/078*** | (2010.01) |
| ***C12N 5/0784*** | (2010.01) |
| ***C12N 5/0786*** | (2010.01) |

(52) U.S. Cl.

CPC .............. *A61K 40/19* (2025.01); *A61K 40/24* (2025.01); *A61K 40/428* (2025.01); *A61K 45/06* (2013.01); *A61P 35/00* (2018.01); *C12N 5/0634* (2013.01); *C12N 5/0639* (2013.01); *C12N 5/0645* (2013.01); *A61K 2039/522* (2013.01)

(58) Field of Classification Search

CPC .. A61K 2039/522; A61K 40/17; A61K 40/19; A61K 40/24; A61K 39/0208; C01K 14/4748; A23V 2400/175; A61P 35/00; C07K 16/1296; C12N 5/0634; C12N 5/0639; C12N 5/0645

See application file for complete search history.

(56) References Cited

U.S. PATENT DOCUMENTS

| | | | |
|---|---|---|---|
| 2004/0228877 | A1 | 11/2004 | Dubensky et al. |
| 2007/0253976 | A1 | 11/2007 | Paterson et al. |
| 2009/0081248 | A1 | 3/2009 | Paterson et al. |

FOREIGN PATENT DOCUMENTS

| | | | |
|---|---|---|---|
| WO | WO 2004/084936 | 10/2004 | |
| WO | WO 2004/110481 | 12/2004 | |
| WO | WO 2005/009463 | 2/2005 | |
| WO | WO 2007/103261 | 9/2007 | |
| WO | WO 2007/130455 | 11/2007 | |
| WO | WO 2008/140812 | 11/2008 | |
| WO | WO2010/008782 | 1/2010 | |
| WO | WO 2010/102140 | 9/2010 | |
| WO | WO-2016011357 A1 * | 1/2016 | ......... A61K 39/0011 |
| WO | WO 2016/191545 | 12/2016 | |
| WO | WO 2019/006116 | 10/2019 | |
| WO | WO-2019206116 A1 * | 10/2019 | ............. C07K 14/77 |

OTHER PUBLICATIONS

Newman et al. "Structure of Barn HI Endonuclease Bound to DNA: Partial Folding and Unfolding on DNA Binding", Aug. 4, 1995, Science, vol. 269, p. 656-663. (Year: 1995).*

Vasquez-Boland et al. "Listeria Pathogenesis and Molecular Virulence Determinants", Jul. 2001, Clinical Microbiology Reviews, vol. 14, No. 3, p. 584-640. (Year: 2001).*

Ito et al. "Seeligeriolysin O, a Cholesterol-Dependent Cytolysin of Listeria seeligeri, Induces Gamma Interferon from Spleen Cells of Mice", Jan. 2003, Infection and Immunity, vol. 71, No. 1, p. 234-241 (Year: 2003).*

Woo et al. "ovalbumin [Gallus gallus]", GenBank: AAB59956.1, Mar. 29, 2007. (Year: 2007).*

Xu et al., "Effective activation of CD11c and anti-tumor immune in immunized mice with recombinant *E. coli.* LLO/OVA," Journal of Third Military Medical University, Journal of Third Military Medical University, 29(17), Sep. 2007, 4 pages (English Abstract only).

Xu et al., "Expressions of cytokines in murine bone marrow dendritic cells stimulated by recombinant *E coli* LLOOVA," Immunological Journal, 23(4), Jul. 2007, 5 pages (English abstract only).

Banchereau et al., "Dendritic cells as therapeutic vaccines against cancer," [J]. Nature Reviews Immunology, 2005, 5:4:296-306.

Couzin-Frankel et al.,"Breakthrough of the year 2013. Cancer immunotherapy," Science, 2013, 342:6165:1432-3.

Gilboa et al., "Immunotherapy of cancer with dendritic-cell-based vaccines," Cancer Immunology, Immunotherapy, 1998, 46(2):82-87.

Jenne, "Dendritic cells containing apoptotic melanoma cells prime human CD8+ T cells for efficient tumor cell lysis," Cancer Research, 2000, 60(16):4446-4452.

Kikuchi et al., Dendritic cells genetically modified to express CD40 ligand and pulsed with antigen can initiate antigen-specific humoral immunity independent of CD4+ T cells, Nature Medicine, 2000, 6(10):1154-1159.

Lanier, "Up on the tightrope: natural killer cell activation and inhibition," Nature Immunology, 2008, 9:5:495-502.

Mellman et al., "Dendritic cells : specialized and regulated antigen processing machines.," [J]. Cell, 2001, 106:255-258.

Nair et al., "Induction of primary carcinoembryonic antigen (CEA)-specific cytotoxic T lymphocytes in vitro using human dendritic cells transfected with RNA," Nature Biotechnology, 1998, 16(4):364-369.

Palucka et al.,"Cancer immunotherapy via dendritic cells," Nature Reviews Cancer, 2012, 12:4:265-277.

PCT International Preliminary Report and Written Opinion in Appln. No. PCT/CN2019/098594, dated Feb. 2, 2021, 6 pages.

Peng et al., "The ability of two listeria monocytogenes vaccines targeting human papillomavirus-16 E7 to induce an antitumor response correlates with myeloid dendritic cell function," The Journal of Immunology, 2004, 6030-6038.

Rosenberg et al., "A new approach to the adoptive immunotherapy of cancer with tumor-infiltrating lymphocytes," Science, 1986, 233(4770):1318-1321.

Rosenberg et al., "Cancer immunotherapy: moving beyond current vaccines," Nature Medicine, 2004, 10:9:909-915.

Sharma et al., "Novel cancer immunotherapy agents with survival benefit: recent successes and next steps," Nature Reviews Cancer, 2011, 11:11:805-812.

Steinman, "The Dendritic Cell System and its Role in Immunogenicity," [Annual Review of Immunology, 1991, 9(1):271-296.

Topalian et al., "Cancer immunotherapy comes of age," J. Nat. Clinical Practice Oncology, 2011,29:36:4828-4836.

Turtle et al., "CD19 CAR-T cells of defined CD4+:CD8+ composition in adult B cell ALL patients," Journal of Clinical Investigation, 2016, 126:6:2123-2138.

(56) References Cited

OTHER PUBLICATIONS

Wang et al., "Comparative study on anti-tumor immune response of autologous cytokine-induced killer(CIK) cells, dendritic cells-CIK(DC-CIK),and semi-allogeneic DC-CIK," Chinese Journal of Cancer, 2010, 29:7:641-648.
Wang et al., "Eliciting T cell immunity against poorly immunogenic tumors by immunization with dendritic cell-tumor fusion vaccines" Journal of Immunology, 1998, 161(10):5516.
Yamamoto et al., "Immunotherapy for Prostate Cancer with Gc Protein-Derived Macrophage-Activating Factor, GcMAF," Translational Oncology, 2008, 1:2:65-72.
Roeske et al., "Delivery of Chicken Egg Ovalbumin to Dendritic Cells by Listeriolysin O-Secreting Vegetative Bacillus subtilis," J. Microbiol., Biotechnol, 2018, 28:1:122-135.
Radford et al., "A Recombinant *E.coli* Vaccine to Promote MHC Class I-dependent Antigen Presentation: Application to Cancer Immunotherapy," Gene Therapy, Dec. 2002, 9(21):1455-1463.
Xu et al., "Effective activation of CD 11c and anti-tumor immune in immunized mice with recombinant *E.coli*. LLO/OV A," ActaAcademiae Medicinae Militaris Tertiae, Sep. 2007, 29(17):1702-1705 (with English abstract).
Jia et al., "Application of Attenuated Listeria Monocyto-genes Vectors in tumor Vaccines," Chinese Journal of Ommunology, Dec. 31, 2016, 32(12):1866, 5 pages (with English abstract).
PCT International Search Report in International Appln. No. PCT/US2019/098594, mailed on Oct. 30, 2019, 12 pages (with English translation).

* cited by examiner

TUMOR IMMUNOTHERAPY COMPOSITION BASED ON ANTIGEN-PRESENTING CELLS ACTIVATED BY ATTENUATED *LISTERIA MONOCYTOGENES*, PREPARATION METHOD THEREFOR AND APPLICATION THEREOF

TECHNICAL FIELD

The present disclosure mainly relates to the field of biotechnology. To be specific, the present disclosure provides a tumor immunotherapy composition based on antigen-presenting cells activated by an attenuated *Listeria* carrying the plasmid of a non-integrative antigen peptide, preparation method therefor and application thereof.

BACKGROUND

In recent years, with the intensive research and understanding of the occurrence and development of tumor, antitumor immune response of the body, tumor immune escape, tumor microenvironment and the like, new ideas and new strategies for tumor immunotherapy have been further studied and explored, and tumor immunotherapy has received unprecedented attention [1]. Since tumor immunotherapy shows incomparable advantages over conventional surgery, radiotherapy and chemotherapy in clinical research, i.e., few damage to the organ(s) of a patient, slight adverse reaction produced in treatment, effective removal of residual tumors, significantly prolonged survival and the like, it is thus considered as a method which is most likely to cure cancer, and was listed as the top of the ten major scientific breakthroughs in 2013 by Science [2]. Currently, the research of tumor immunotherapy mainly focuses on aspects of immune checkpoint inhibitors, therapeutic antibodies, tumor vaccines, cellular immunotherapy, small molecule inhibitors and the like.

Currently, common cellular immunotherapies include autologous tumor infiltrating lymphocytes (TIL), NK cell (Natural killer cell)-based immunotherapy, DC-CIK, macrophage activation therapy, CAR-T (chimeric antigen receptor T cell), and the like [3-7]. Autologous tumor infiltrating lymphocytes are lymphocytes that are isolated from tumor sites and then proliferated and generated after the stimulation with cytokines such as IL-2 in vitro. The phenotypes of autologous tumor infiltrating lymphocytes are mainly $CD4^+$ T cells and $CD8^+$T cells. Despite their strong cell proliferative ability and killing effect in clinical practice, autologous tumor infiltrating lymphocytes show restriction in tumor type and MHC restriction to some extent, the collection of cells is restricted and the process is cumbersome. NK cell-based immunotherapy has been used in clinical research on melanoma and lung cancer, etc. Unlike T cells, no tumor-specific recognition or proliferation is required before the exhibition of antitumor response. However, the antitumor effect of NK cells is controlled by a large number of receptors on the surface of tumor cells, resulting in low efficiency in clinical practice. DC-CIK cell therapy is a method of treating tumor by using DC (dendritic cell) and CIK (cytokine-induced killer) cell in combination. Since DC-CIK cell therapy is not restricted by factors such as MHC, it has broad-spectrum antitumor effect in theory and is applied to the treatment of a variety of cancers at different stages in China. However, such method has been found to be less effective in clinical studies in the United States for decades. Meanwhile, the preparation process of the aforementioned cells is difficult to control and has poor reproducibility. Macrophage activation therapy is a therapeutic method developed by Japanese scientists to activate macrophages in human body. This method utilizes GcMAF as an immune stimulant to activate macrophages, thereby achieving antitumor benefits. However, this method has poor antitumor effect due to the lack of tumor specificity. CAR-T therapy is currently the only FDA-approved therapeutic method with excellent clinical effects. Its principle is to enable the expression of chimeric receptors capable of binding to specific tumor antigens on the surface of T cells and introducing a signal transmission region causing the activation of T cells in the intracellular segment of the receptor at the same time by subjecting T cells collected from the patient's own blood to genetic engineering process, thus enabling the reinfused cells capable of killing tumor cells with corresponding antigens. This therapy is not restricted by MHC and therefore shows good targeting ability, killing ability and durability in clinical trials. However, this method is merely suitable for hematological cancers at present and has not exerted good effects in clinical studies of solid tumors. In addition, this method also has unique side effects such as cytokine storm, which needs to be solved urgently [8-10].

As with the intensive research on tumor immunotherapy, in a therapeutic regimen based on enhancing the production of immune response of tumor-specific killing in body, whether effective antigen presentation is proceeded in the body is directly related to the therapeutic effect [11-12]. Dendritic cells (DC) are antigen-presenting cells with the most powerful functions ever found so far, and have functions such as phagocytosis, antigen processing, antigen presentation and stimulating T cells to produce specific tumor immune response [13]. Therefore, the therapeutic strategy of activating tumor-specific immune response by cultivating the autologous DCs of the patient in virto, constructing a DC tumor vaccine via various means, and then reinfusing the DC tumor vaccine into the body has become another new therapeutic method following surgery, radiotherapy and chemotherapy and other therapeutic means [9, 14]. The method for in-vitro treatment and activation of DC tumor vaccine is the key point in its use in antitumor immunotherapy, and the construction methods of DC tumor vaccine are mainly as follows. ① Sensitized DCs are produced by treatment with lysate of tumor cells, that is, tumor cells are lysed to release tumor antigens via physical or chemical means, and then a vaccine is constructed by treating DCs with the tumor antigens. This method needs a large amount of intratumoral tissue and the composition of the lysate is complex. The lysate contains the normal antigens of the body, which may form a variety of antigen epitopes. Such method has less specificity and has the risk of inducing autoimmune diseases. Besides, the clinical effectiveness of the treatment needs to be further studied [15]; ② DC-tumor cell fusion vaccine. That is, patient's autologous tumor cells cultured in vitro are fused with DC to generate hybrid cells which are then reinfused into the body after purification and isolation, thereby being capable of effectively inducing tumor-specific killing. However, due to relatively low fusion efficiency and lack of effective method for isolation and purification, it is difficult to obtain a sufficient amount of high-quality hybrid cells, which affects clinical efficacy [16]. ③ DC tumor vaccine with antigen gene(s) introduced therein. That is, the tumor vaccine is constructed by introducing a tumor-associated antigen or a tumor-specific antigen into DC by means of gene transfection or virus. This method is capable of realizing the effective presentation of antigens, but there are processes such as the introduction of exogenous gene(s) and genetic modification, which require more safety verification and standardized standards for processes [17]; ④ Treatment with tumor antigen polypeptide(s) or protein(s). That is, the antitumor immune response is activated by treating DC cells with tumor-specific polypeptide(s) or protein antigen(s) synthesized in vitro and enabling the accomplishment of phagocytosis and antigen presentation by DC. This method has good targeting ability and effectiveness and is easy for survival detection. However, it requires the acquisition of the HLA subtype of the patient, the prediction of the polypeptide sequence(s) recognized by the patient, and the like, so as to carry out the matching of effective polypeptide(s). The recognition and effective presentation of each polypeptide by DC upon the impact of multi-target antigen polypeptides on DC still need to be demonstrated [18].

Since the above problems still remain in existing cellular immunotherapeutic schemes, a novel tumor immunotherapy composition, method and application need to be developed to solve the problems of complicated operation process and risks regarding targeting ability and safety.

PRIOR ART LITERATURES

[1] Topalian S L, Weiner G J, Pardoll D M. Cancer immunotherapy comes of age. [J]. Nature Clinical Practice Oncology, 2011, 2(3):115.

[2] Couzinfrankel J. Breakthrough of the year 2013. Cancer immunotherapy. [J]. Science, 2013, 342(6165):1432-3.

[3] Rosenberg S A, Spiess P, Lafreniere R. A new approach to the adoptive immunotherapy of cancer with tumor-infiltrating lymphocytes. [J]. Science, 1986, 233(4770): 1318-1321.

[4] Lanier L L. Up on the tightrope: natural killer cell activation and inhibition. [J]. Nature Immunology, 2008, 9(5):495-502.

[5] Wang Q J, Wang H, Pan K, et al. Comparative study on anti-tumor immune response of autologous cytokine-induced killer (CIK) cells, dendritic cells-CIK (DC-CIK), and semi-allogeneic DC-CIK [J]. Chinese Journal of Cancer, 2010, 29(7):641-648.

[6] Yamamoto N, Suyama H, Yamamoto N. Immunotherapy for Prostate Cancer with Gc Protein-Derived Macrophage-Activating Factor, GcMAF [J]. Translational Oncology, 2008, 1(2):65-72.

[7] Turtle C J, Hanafi L A, Berger C, et al. CD19 CAR-T cells of defined CD4+: CD8+ composition in adult B cell ALL patients [J]. Journal of Clinical Investigation, 2016, 126(6):2123-2138.

[8] Sharma P, Wagner K, Wolchok J D, et al. Novel cancer immunotherapy agents with survival benefit: recent successes and next steps [J]. Nature Reviews Cancer, 2011, 11(11):805-812.

[9] Rosenberg S A, Yang J C, Restifo N P. Cancer immunotherapy: moving beyond current vaccines [J]. Nature Medicine, 2004, 10(9):909-915.

[10] Palucka K, Banchereau J. Cancer immunotherapy via dendritic cells [J]. Nature Reviews Cancer, 2012, 12(4): 265-277.

[11] Mellman I. Dendritic cells: specialized and regulated antigen processing machines [J]. Cell, 2001, 106.

[12] Banchereau J, Palucka A K. Dendritic cells as therapeutic vaccines against cancer [J]. Nature Reviews Immunology, 2005, 5(4):296-306.

[13] Steinman, Ralph M. The Dendritic Cell System and its Role in Immunogenicity [J]. Annual Review of Immunology, 1991, 9(1):271-296.

[14] Gilboa E, Nair S K, Lyerly H K. Immunotherapy of cancer with dendritic-cell-based vaccines [J]. Cancer Immunology, Immunotherapy, 1998, 46(2):82-87.

[15] Jenne L. Dendritic cells containing apoptotic melanoma cells prime human CD8+ T cells for efficient tumor cell lysis. [J]. Cancer Research, 2000, 60(16):4446-4452.

[16] Wang J, Saffold S, Cao X, et al. Eliciting T cell immunity against poorly immunogenic tumors by immunization with dendritic cell-tumor fusion vaccines. [J]. Journal of Immunology, 1998, 161(10):5516.

[17] Nair S K, Boczkowski D, Morse M, et al. Induction of primary carcinoembryonic antigen (CEA)-specific cytotoxic T lymphocytes in vitro using human dendritic cells transfected with RNA [J]. Nature Biotechnology, 1998, 16(4):364-369.

[18] Kikuchi T, Worgall S, Singh R, et al. Dendritic cells genetically modified to express CD40 ligand and pulsed with antigen can initiate antigen-specific humoral immunity independent of CD4+ T cells. [J]. Nature Medicine, 2000, 6(10):1154-1159.

SUMMARY

Problems to be Solved by the Disclosure

The present disclosure provides a tumor immunotherapeutic method based on antigen-presenting cells activated by an attenuated *Listeria* carrying the plasmid of a non-integrative antigen peptide. An attenuated *Listeria* carrying the plasmid of a specific antigen is utilized to activate antigen-presenting cells, thereby activating the function of antigen presentation by MHC and a series of in-vivo cellular immune responses to achieve the purpose of antitumor therapy. The advantages of this method are as below. It is able to specifically activate antigen-presenting cells and thus triggers a series of specific antitumor immune responses. Meanwhile, the operation process requires no genetic modification of autologous cells and is not restricted by the type of tumors, and the overall process is simple and easy to operate and is reproducible, thereby enabling the activation of a series of antitumor immune responses in vivo and significant improvement of targeting ability and safety.

Means for Solving the Problems

The technical solutions involved in the present disclosure are as follows.

(1) A modified cell obtained by contacting a cell having an activity for producing a target effect with a recombinant *Listeria*, wherein said recombinant *Listeria* comprises (i) a recombinant nucleic acid molecule, or (ii) a recombinant plasmid, or (iii) a recombinant expression vector; or said recombinant *Listeria* expresses (iv) a recombinant protein; wherein said (i) recombinant nucleic acid molecule comprises an open reading frame encoding a recombinant polypeptide, said recombinant polypeptide comprises a heterologous antigen fused to a derived Listeriolysin O (LLO) polypeptide, said recombinant nucleic acid molecule further comprises a first promoter sequence; wherein said derived Listeriolysin O (LLO) polypeptide is selected from: a polypeptide represented by an amino acid sequence as set forth in SEQ ID NO:4, or polypeptides that are obtained by substitution, repetition, deletion or addition of one or more amino acids in the amino acid sequence as set forth in SEQ ID NO:3 and have or partially have the activity of an Listeriolysin O (LLO) polypeptide as set forth in SEQ ID NO:2;

said (ii) recombinant plasmid or (iii) said recombinant expression vector comprises the sequence of said (i) recombinant nucleic acid molecule;

said (iv) recombinant protein is encoded by said (i) recombinant nucleic acid molecule, or is expressed by said (ii) recombinant plasmid or said (iii) recombinant expression vector;

wherein said cell having an activity for producing a target effect is selected from antigen-presenting cells.

(2) The modified cell according to (1), wherein, alternatively, said antigen-presenting cell is a macrophage and/or a dendritic cell; preferably, said macrophage is a bone marrow-derived macrophage; preferably, said dendritic cell is a bone marrow-derived dendritic cell.

(3) The modified cell according to (1), wherein in said (i) recombinant nucleic acid molecule, an amino acid sequence of said derived Listeriolysin O (LLO) polypeptide has at least 80% identity, preferably at least 90% identity, more preferably at least 95% identity and most preferably at least 97% identity with the amino acid sequence encoding an Listeriolysin O (LLO) polypeptide as set forth in SEQ ID NO: 2.

(4) The modified cell according to any one of (1) to (3), wherein in said (i) recombinant nucleic acid molecule, said heterologous antigen is selected from tumor antigens or non-tumor antigens; alternatively, said non-tumor antigens are selected from OVA or fragments having the function of OVA.

(5) The modified cell according to (4), wherein in said (i) recombinant nucleic acid molecule, an amino acid sequence of said OVA or an amino acid fragment having the function of OVA comprises an amino acid sequence as set forth in SEQ ID NO:7; preferably, a nucleotide sequence encoding said OVA or said amino acid fragment having the function of OVA comprises a nucleotide sequence as set forth in SEQ ID NO:6.

(6) The modified cell according to any one of (1) to (3), wherein a linking sequence is further comprised in said (i) recombinant nucleic acid molecule, said linking sequence links a nucleotide sequence encoding said derived Listeriolysin O (LLO) polypeptide and a nucleotide sequence encoding said heterologous antigen; alternatively, in said (i) recombinant nucleic acid molecule, said linking sequence comprises a nucleotide sequence encoding a sequence as set forth in SEQ ID NO: 10; preferably, said linking sequence comprises one, two, or three or more repetitions of the sequence as set forth in SEQ ID NO:10.

(7) The modified cell according to (6), wherein in said (i) recombinant nucleic acid molecule, an amino acid sequence, encoded by a nucleotide sequence which is connected to the nucleotide sequence encoding said derived Listeriolysin O (LLO) polypeptide and comprises said linking sequence and the nucleotide sequence of said heterologous antigen, is as set forth in SEQ ID NO:11.

(8) The modified cell according to any one of (1) to (7), wherein in said (i) recombinant nucleic acid molecule, said first promoter sequence is a sequence encoded by Phly gene; alternatively, said recombinant nucleic acid molecule further comprises a tag sequence for detection or a gene encoding a metabolite; preferably, said metabolite is selected from secondary metabolites.

(9) A pharmaceutical composition comprising a therapeutically effective amount of the modified cells according to any one of (1) to (8), wherein, alternatively, said pharmaceutical composition further comprises a second therapeutic agent and/or a pharmaceutically acceptable carrier; preferably, said second therapeutic agent is selected from a second anticancer agent; more preferably, said second anticancer agent is selected from a second recombinant *Listeria*, a radiotherapeutic agent, a chemotherapeutic agent or an immunotherapeutic agent.

(10) A prophylactic or therapeutic vaccine, wherein said vaccine comprises a prophylactically or therapeutically effective amount of the modified cells according to any one of (1) to (8); alternatively, said vaccine may further comprise an immunologic stimulant; preferably, said immunologic stimulant is selected from adjuvants.

(11) Use of the modified cell according to any one of (1) to (8) or the pharmaceutical composition of (9) in preparation of a drug for killing cells.

(12) The use according to (11), wherein said cells are contained in a patient; alternatively, said cells are selected from proliferative cells, neoplastic cells, precancerous cells or metastatic cells; preferably, said cells are selected from metastatic cells; more preferably, the metastatic cells are selected from metastatic tumor cells.

(13) Use of the modified cell according to any one of (1) to (8), the pharmaceutical composition of (9) or the vaccine of (10) in preparation of a drug for treating or preventing a tumor in a tumor patient.

(14) A method for slowly and continuously killing cells, comprising contacting said cells with the modified cell of any one of (1) to (8), the pharmaceutical composition of (9) or the vaccine of (10).

(15) The method according to (14), wherein said cells are contained in a patient; alternatively, said cells are selected from proliferative cells, neoplastic cells, precancerous cells or metastatic cells; preferably, said cells are selected from metastatic cells; more preferably, the metastatic cells are selected from metastatic tumor cells.

(16) The method according to (15), wherein said cells and the modified cell of any one of (1) to (8), the pharmaceutical composition of (9) or the vaccine of (10) are administered into a patient.

(17) The method according to (16), wherein the modified cell of any one of (1) to (8), the pharmaceutical composition of (9) or the vaccine of (10) may be administered via oral administration, intraperitoneal administration, intravenous administration, intraarterial administration, intramuscular administration, intradermal administration, subcutaneous administration, transdermal administration, nasal administration, transrectal administration, intratumoral injection, intratumoral indwelling, intra-neurilemma injection, subarachnoid injection or systemic administration; alternatively, said systemic administration includes intravascular administration; preferably, said intravascular administration is selected from injection and perfusion.

(18) The method according to (16) or (17), wherein said method further comprises administering a second anticancer therapy; preferably, said second anticancer therapy may be a chemotherapy, a radiotherapy, an immunotherapy, a surgical therapy, or a combination of one or more of the above-mentioned therapies.

(19) A method for inducing an immune response in a subject, wherein said method comprises administering the modified cell of any one of (1) to (8), the pharmaceutical composition of (9) or the vaccine of (10) to the subject.

(20) A method for activating a cell having an activity for producing a target effect, wherein said cell having an activity for producing a target effect is brought into contact with the recombinant *Listeria* of any one of (1) to (8), wherein said contact occurs in vitro; alternatively, said cell having an activity for producing a target effect is selected from antigen-presenting cells; alternatively, said antigen-presenting cell is a macrophage and/or a dendritic cell; preferably, said macrophage is a bone marrow-derived macrophage; preferably, said dendritic cell is a bone marrow-derived dendritic cell.

Advantageous Effects of the Disclosure

In one embodiment, an immunotherapeutic method based on antigen-presenting cells activated by an attenuated *Listeria* is established in the present disclosure. This method utilizes the antigens of different types of tumors carried by the attenuated *Listeria* constructed in vitro and the antigen-presenting property of the antigen-presenting cells to quickly obtain antigen-presenting cells capable of presenting specific tumor antigen peptide in vitro, which are then reinfused into the body to achieve tumor-specific immune responses.

In one embodiment, a tumor immunotherapeutic method based on macrophages activated by an attenuated *Listeria* carrying the plasmid of a non-integrative antigen peptide is established in the present disclosure. By utilizing the antigens of different types of tumors carried by the attenuated *Listeria* constructed in vitro and the antigen-presenting property of macrophages, macrophages cultured and proliferated in vitro are stimulated by the attenuated *Listeria* carrying the plasmid of the non-integrative antigen peptide to obtain macrophages presenting specific tumor antigen peptide, which are then reinfused into the body to achieve a series of tumor-specific immune responses. This method is not restricted by the type of tumor, the overall process is simple and convenient to operate, the conditions are highly controllable, and the method is reproducible, thereby enabling the significant activation of antitumor immune response in vivo and definitely securing the targeting ability and safety.

In one embodiment, a tumor immunotherapeutic method based on dendritic cells activated by an attenuated *Listeria* carrying the plasmid of a non-integrative antigen peptide is established in the present disclosure. By utilizing the antigens of different types of tumors carried by the attenuated *Listeria* constructed in vitro and the antigen-presenting property of dendritic cells, dendritic cells cultured and proliferated in vitro are stimulated by the attenuated *Listeria* carrying the plasmid of the non-integrative antigen peptide to obtain dendritic cells presenting specific tumor antigen peptide, thus activating MHC class I and MHC class II antigen presentation and a series of in-vivo cellular immune responses. The resulted dendritic cells are then reinfused into the body to achieve a series of tumor-specific immune responses. This method is not restricted by the type of tumor, the overall process is simple and convenient to operate, the conditions are highly controllable, and the method is reproducible, thereby enabling the significant activation of antitumor immune response in vivo and definitely securing the targeting ability and safety.

In one embodiment, the effectiveness of antigen presentation by antigen-presenting cells can be ensured by a 30-min in-vitro treatment with an attenuated *Listeria* carrying the plasmid of a non-integrative antigen peptide in the present disclosure, which greatly shortens the treatment process.

In one embodiment, the present disclosure uses an inactivated attenuated *Listeria* to bind antigen-presenting cells, and such method is also capable of causing antitumor immune response to some extent, which greatly improves safety.

BRIEF DESCRIPTION OF THE DRAWINGS

FIG. 7A shows the results of the positive control group wherein untreated BMDMs and OT1 $CD8^+$ T cells are co-cultured (containing 10 ng/μl OVA polypeptide); FIG. 7B shows the results of the negative control group wherein untreated BMDMs and OT1 $CD8^+$ T cells are co-cultured; FIG. 7C shows the results of LM-LLO540 experimental group (MOI: 0.5) wherein BMDMs are treated with LM-LLO540 at an MOI of 0.5 for 30 minutes and then co-cultured with OT1 $CD8^+$ T cells; FIG. 7D shows the results of LM-LLO540 experimental group (MOI: 0.1) wherein BMDMs are treated with LM-LLO540 at an MOI of 0.1 for 30 minutes and then co-cultured with OT1 $CD8^+$ T cells; FIG. 7E shows the results of LM-LLO540 experimental group (MOI: 0.01) wherein BMDMs are treated with LM-LLO540 at an MOI of 0.01 for 30 minutes and then co-cultured with OT1 $CD8^+$ T cells; FIG. 7F shows the results of LM-LLO540-OVA28 experimental group (MOI: 0.5) wherein BMDMs are treated with LM-LLO540-OVA28 at an MOI of 0.5 for 30 minutes and then co-cultured with OT1 $CD8^+$ T cells; FIG. 7G shows the results of LM-LLO540-OVA28 experimental group (MOI: 0.1) wherein BMDMs are treated with LM-LLO540-OVA28 at an MOI of 0.1 for 30 minutes and then co-cultured with OT1 $CD8^+$ T cells; FIG. 7H shows the results of LM-LLO540-OVA28 experimental group (MOI: 0.01) wherein BMDMs are treated with LM-LLO540-OVA28 at an MOI of 0.01 for 30 minutes and then co-cultured with OT1 $CD8^+$ T cells.

DETAILED DESCRIPTION

Definitions

Figure 1:
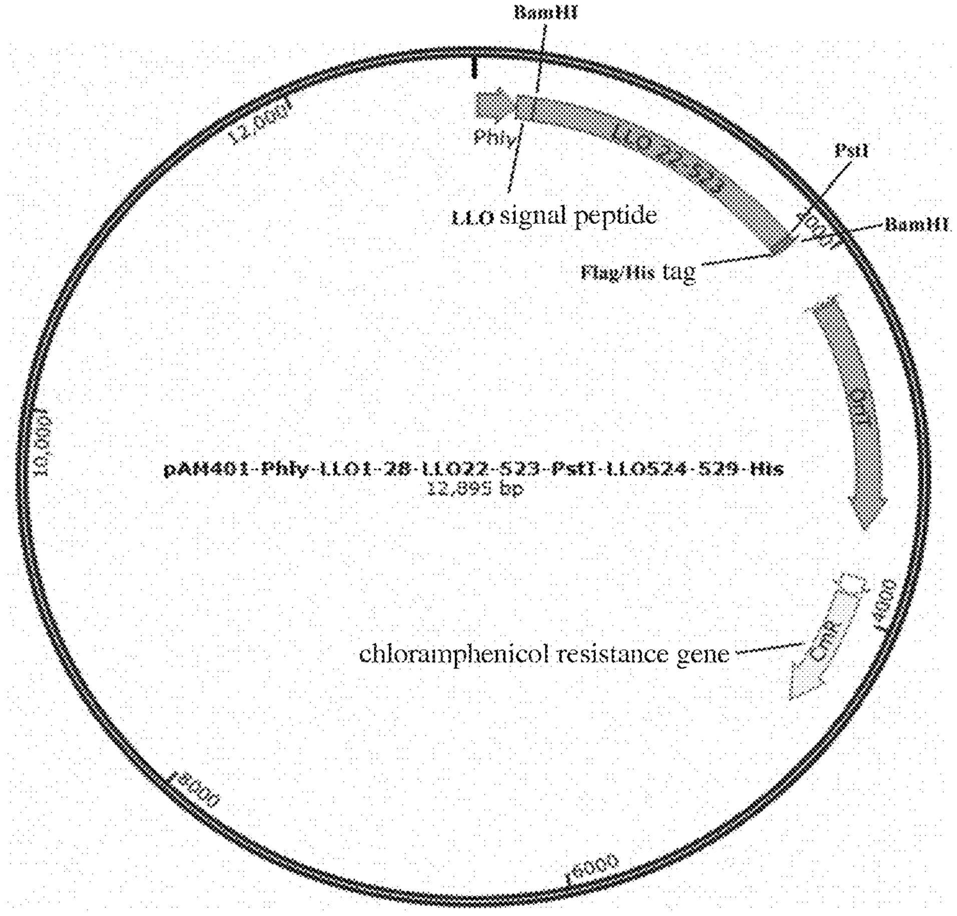
FIG. 1 shows the profile of the plasmid of the *Listeria* expressing the antigen gene.

When used in combination with the term "comprise" in claims and/or specification, the wording "a" or "an" may refer to "one", but may also refer to "one or more", "at least one" and "one or more than one".

As used in claims and specification, the wording "comprise", "have", "include" or "contain" means inclusive or open-ended, and does not exclude additional and unreferenced elements, method or steps. Meanwhile, the wording "comprise", "have", "include" or "contain" may also mean close-ended, excluding additional and unreferenced elements, method or steps.

Throughout the application document, the term "about" means that a value includes the standard deviation of the error of the device or method used to determine the value.

Although the definition of the term "or" as being an alternative only and as "and/or" are both supported by the disclosed content, the term "or" in claims means "and/or" unless it is explicitly indicated that the term "or" only means an alternative or the alternatives are mutually exclusive.

When used in claims or specification, the selected/alternative/preferred "numerical range" includes both the numerical endpoints at both ends of the range and all natural numbers covered by the range between said numerical endpoints with respect to the aforementioned numerical endpoints.

When used in claims and/or specification, the term "inhibition", "reduction", "prevention" or any variation of these terms includes any measurable reduction or complete inhibition for the purpose of achieving the desired results (for example, treatment of cancer). Desired results include but are not limited to the relief, reduction, slowing or eradication of a cancer, a hyperproliferative condition or a symptom related to a cancer, as well as the improved quality or extension of life.

The vaccination method in the present disclosure may be used for treating cancers in a mammal. The term "cancer" used in the present disclosure includes any cancer, including but not limited to melanoma, sarcoma, lymphoma, cancer (for example, brain cancer, breast cancer, liver cancer, gastric cancer, lung cancer, and colon cancer) and leukemia.

The term "mammal" in the present disclosure refers to human and non-human mammals.

The method of the present disclosure comprises administering to a mammal a vaccine comprising a tumor antigen to which the mammal has pre-existing immunity. The term "pre-existing immunity" used in the present disclosure is intended to include the immunity induced by vaccination with an antigen and the immunity naturally existing in a mammal.

The term "OVA" in the present disclosure refers to ovalbumin (also referred to as chicken ovalbumin), which consists of 386 amino acids and has a molecular weight of approximately 45 kD.

The term "Phly" in the present disclosure is the promoter of the gene encoding LLO (Listeriolysin O).

The term "vaccine" in the present disclosure refers to an immune formulation for preventing diseases prepared by methods such as artificially attenuating, inactivating or genetically modifying pathogenic microorganisms (such as bacteria) and the metabolites thereof.

The term "antigen-presenting cell" in the present disclosure includes dendritic cells and macrophages. Among them, dendritic cells are capable of significantly stimulating the proliferation of naive T cells, and are the initiators of the body's immune response and the only antigen-presenting cells capable of activating naive T cells, while macrophages are capable of stimulating T cells that have been activated.

In the present disclosure, the wording "treat" means that allowing the subject to contact with (for example, be administered with) the strains and/or macrophages of the present disclosure or a pharmaceutical composition containing them (hereinafter also referred to as "the pharmaceutical composition of the present disclosure") after suffering from a disease so as to alleviate the symptom(s) of the disease compared to the situation where no such contact is allowed. However, the wording "treat" does not mean that the symptom(s) of the disease must be completely suppressed. Suffering from a disease refers to the occurrence of symptom(s) of the disease in the body.

In the present disclosure, the wording "prevent" means that allowing the subject to contact with (for example, be administered with) the pharmaceutical composition and the like of the present disclosure before suffering from a disease so as to alleviate the symptom(s) of the disease after suffering from the disease compared to the situation where no such contact is allowed. However, the wording "prevent" does not mean that it is necessary to completely prevent the subject from suffering the disease.

The term "radiotherapeutic agent" in the present disclosure includes drugs that cause DNA damage. Radiotherapy has been widely used in the treatment of cancer and diseases, and includes those commonly referred to as γ-ray and X-ray and/or targeted delivery of radioisotopes to tumor cells.

The term "chemotherapeutic agent" in the present disclosure is a chemical compound useful for treating cancer. Classes of chemotherapeutic agents include but are not limited to: an alkylating agent, an antimetabolite, a kinase inhibitor, a spindle poison plant alkaloid, a cytotoxic/antitumor antibiotic, a topoisomerase inhibitor, a photosensitizer, an anti-estrogen, a selective estrogen receptor modulator, an anti-progesterone, an estrogen receptor downregulator, an estrogen receptor antagonist, a luteinizing hormone-releasing hormone agonist, anti-androgens, an aromatase inhibitor, an EGFR inhibitor, a VEGF inhibitor, an antisense oligonucleotide that inhibits the expression of gene(s) involved in abnormal cell proliferation or tumor growth. Chemotherapeutic agents that may be used in the treatment method of the present disclosure include a cell growth inhibitor and/or a cytotoxic agent.

The term "immunotherapeutic agent" in the present disclosure comprises an "immunomodulator" and an agent that facilitates or mediates an antigen presentation that increases a cell-mediated immune response. Among them, the "immunomodulator" comprises an immune checkpoint modulator. For example, immune checkpoint protein receptors and their ligands mediate the suppression of T cell-mediated cytotoxicity and are often expressed by tumors or expressed on anergic T cells in the tumor microenvironment, thus permitting the tumor to evade immune attack. Inhibitors of the activity of immunosuppressive checkpoint protein receptors and their ligands may overcome the immunosuppressive tumor environment, so as to permit cytotoxic T cell attack on tumor. Examples of immune checkpoint proteins include but are not limited to PD-1, PD-L1, PDL2, CTLA4, LAG3, TIM3, TIGIT and CD103. Modulation (including inhibition) of the activity of such protein may be accomplished by an immune checkpoint modulator, which may include, for example, an antibody, an aptamer, a small molecule, a soluble form of a checkpoint receptor protein and the like that target a checkpoint protein. PD-1-targeting inhibitors include the approved drug agents pembrolizumab and nivolumab, while ipilimumab is an approved CTLA-4 inhibitor. Antibodies specific for PD-L1, PD-L2, LAG3, TIM3, TIGIT and CD103 are known and/or commercially available, and may also be produced by those skilled in the art.

The term "substitution, repetition, deletion or addition of one or more amino acids" in the present disclosure includes a "conservative mutation". The term "conservative mutation" in the present disclosure refers to a conservative mutation capable of normally maintaining the function of the protein. A representative example of conservative mutations is conservative substitution. Conservative substitution refers to, for example, a mutation wherein substitution takes place mutually among Phe, Trp and Tyr in a case where the substitution site is an aromatic amino acid; a mutation wherein substitution takes place mutually among Leu, Ile and Val in a case where the substitution site is a hydrophobic amino acid; a mutation wherein substitution takes place mutually between Gln and Asn in a case where the substitution site is a polar amino acid; a mutation wherein substitution takes place mutually among Lys, Arg and His in a case where the substitution site is a basic amino acid; a mutation wherein substitution takes place mutually between Asp and Glu in a case where the substitution site is an acidic amino acid; and a mutation wherein substitution takes place mutually between Ser and Thr in a case where the substitution site is an amino acid having a hydroxyl group. As substitutions considered as conservative substitutions, there may be specifically exemplified substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. In addition, the conservative mutations also include naturally occurring mutations which are attributed to the individual-derived gene differences, difference in strains, difference in species and the like.

The term "bone marrow-derived macrophage" in the present disclosure is also referred to as BMDM, which is a primary cell obtained by the stimulation and induction of bone marrow cells by specific growth factor(s).

The term "bone marrow-derived dendritic cell" in the present disclosure is also referred to as BMDC, which is a primary cell obtained by the stimulation and induction of bone marrow cells by specific growth factor(s).

The term "ELISPOT" in the present disclosure has a full name of enzyme-linked immunospot assay, which combines cell culture technology and enzyme-linked immunosorbent technology and is capable of detecting the cytokine secreted by a single cell.

This method enables the appearance of clear and recognizable spots at the corresponding positions where cells secrete soluble proteins. Such spots may be manually counted directly under a microscope or counted by an ELISPOT analysis system, so as to calculate the frequency of cells secreting the protein or cytokine.

The strain "LM-LLO540-OVA28" in the present disclosure refers to LM 10403SΔactA (pAM401-Phly-$LLO_{1-28}$-$LLO_{22-523}$-$(G4S)_2$-$OVA_{28}$-$(G4S)_2$-$LLO_{524-529}$-His).

The strain "LM-LLO540" in the present disclosure refers to LM 10403SΔactA (pAM401-Phly-$LLO_{1-28}$-$LLO_{22-267}$-PstI-$LLO_{524-529}$-His), which may be also represented as LM 10403SΔactA (pAM401-Phly-$LLO_{540}$-His).

As for the "conventional biological methods in this field" in the present disclosure, please refer to the corresponding methods described in the public publications such as "Current Protocols in Molecular Biology" published by Wiley, "Molecular Cloning: A Laboratory Manual" published by Cold Spring Harbor Laboratory.

Technical Solutions

In the embodiments of the present disclosure, the meanings of SEQ ID NOs in the nucleotide and amino acid sequence lists of the specification are as follows.

The sequence as set forth in SEQ ID NO:1 is the nucleotide sequence of the wild-type Listeriolysin O (LLO) ($LLO_{529}$).

The sequence as set forth in SEQ ID NO:2 is the amino acid sequence of the wild-type Listeriolysin O (LLO) ($LLO_{529}$).

The sequence as set forth in SEQ ID NO:3 is the nucleotide sequence of the recombinant Listeriolysin O (LLO) ($LLO_{540}$).

The sequence as set forth in SEQ ID NO:4 is the amino acid sequence of the recombinant Listeriolysin O (LLO) ($LLO_{540}$).

The sequence as set forth in SEQ ID NO:5 is an unoptimized nucleotide sequence of $OVA_{28}$.

The sequence as set forth in SEQ ID NO:6 is an optimized nucleotide sequence of $OVA_{28}$.

The sequence as set forth in SEQ ID NO:7 is an optimized amino acid sequence of $OVA_{28}$.

The sequence as set forth in SEQ ID NO:8 is a nucleotide sequence of which the 5'-end is homologous to the 5'-end of its corresponding sequence.

The sequence as set forth in SEQ ID NO:9 is a nucleotide sequence of which the 3'-end is homologous to the 3'-end of its corresponding sequence.

The sequence as set forth in SEQ ID NO: 10 is the amino acid sequence of the linking sequence.

The sequence as set forth in SEQ ID NO:11 is an amino acid sequence wherein the amino acid sequence of $OVA_{28}$ is linked to the linking sequence.

In one embodiment of the present disclosure, said Listeriolysin O (LLO) polypeptide has at least 80%, 81%, 82%, 83%, 84%, 85%, 86%, 87%, 88%, 89%, 90%, 91%, 92%, 93%, 94%, 95%, 96%, 97%, 98%, 99%, 100% (including all ranges and percentages between these values) amino acid identity with the amino acid sequence as set forth in SEQ ID NO:1. The above-mentioned Listeriolysin O (LLO) polypeptides having a certain percentage of identity means that Listeriolysin O (LLO) polypeptides have conservative mutations capable of normally maintaining the function of the protein.

In one embodiment of the present disclosure, said Listeriolysin O (LLO) polypeptide is the polypeptide encoded by the sequence as set forth in SEQ ID NO:3.

In one embodiment of the present disclosure, said modified cell has the activity for producing a target effect. In one embodiment, the modified cell has the activity for producing a target effect against an antigen on a target cell. In another embodiment, the activity for producing a target effect includes, but is not limited to, phagocytosis, cytotoxicity on target cells, antigen presentation and cytokine secretion.

In one embodiment of the present disclosure, in order to develop the pre-existing immunity, the method of the present disclosure comprises a step of vaccinating a mammal with a heterologous antigen suitable for inducing immune response against target cancer cells. In one example, said heterologous antigen is selected from tumor antigens. For example, the tumor antigen may be a tumor-associated antigen (TAA), such as a substance generated in tumor cells that trigger an immune response in a mammal. Examples of such antigens include oncofetal antigens (such as alpha-fetoprotein (AFP)) and carcinoembryonic antigen (CEA), surface glycoproteins (such as CA 125), oncogenes (such as Her2), melanoma-associated antigens (such as dopachrome tautomerase (DCT)), GP100 and MARTI, cancer-testis antigens (such as MAGE protein and NY-ESO1), viral oncogenes (such as HPV E6 and E7), and proteins that are ectopically expressed in tumors and are usually limited to embryonic tissues or extra-embryonic tissues (such as PLAC1). As those skilled in the art should understand, antigen(s) may be selected according to the type of cancer to be treated by the method of the present disclosure since one or more antigens may be particularly suitable for treating certain cancers. For example, as for the treatment of melanoma, a melanoma-associated antigen such as DCT may be used. In another example, said heterologous antigen is selected from non-tumor antigens. For example, the non-tumor antigen is OVA.

An antigen itself may be administered, or preferably, an antigen may be administered via a vector such as an adenovirus (Ad) vector, a poxvirus vector or a retroviral vector, a plasmid, or an antigen-loaded antigen-presenting cell such as a dendritic cell. The method of introducing an antigen into a vector is known to those skilled in the art. In general, the vector may be modified to express the antigen. In this regard, the widely accepted recombination technique is used to integrate the nucleic acid fragment encoding the selected antigen into the selected vector.

An antigen or a vaccine is administered to a mammal by any one of the several methods below, including but not limited to intravenous administration, intramuscular administration or intranasal administration. As those skilled in the art should understand, an antigen or a vector loaded with an antigen may be administered in a suitable vehicle (such as saline or other suitable buffer solutions). After vaccinated with the selected tumor antigen, the mammal produces an immune response within the interval of immune response, for example, the immune response may be produced within about 4 days and last for up to several months, several years or possibly the whole lifetime.

The method of the present disclosure may further include administering a second anticancer therapy, such as a second therapeutic virus. In other aspects, the second anticancer therapy is administering a chemotherapeutic agent, a radiotherapeutic agent or an immunotherapeutic agent, surgery, or the like.

In another aspect, said composition is a pharmaceutically acceptable composition. Said composition may further comprise a second anticancer agent, such as a chemotherapeutic agent, a radiotherapeutic agent or an immunotherapeutic agent.

In another aspect, in addition to the strains and/or macrophages of the present disclosure, the pharmaceutical composition of the present disclosure may comprise a pharmaceutically acceptable carrier. A "pharmaceutically acceptable carrier" refers to any carrier (a liposome, a lipid vesicle, a micelle, etc.), a diluent, an excipient, a wetting agent, a buffer agent, a suspending agent, a lubricant, an adjuvant, an emulsifier, a disintegrating agent, an absorbent, a storage agent, a surfactant, a coloring agent, a flavoring agent or a sweetening agent, which is suitable for a pharmaceutical composition for an immune disease.

The pharmaceutical composition and the like of the present disclosure may be used in a dosage form such as an injection, a freeze-dried product, a tablet, a hard capsule, a soft capsule, a granule, a powder, a pill, a syrup, a suppository, a cataplasm, an ointment, a cream, and an eye drop. Liquid preparations such as injections may be in form of a ready-to-use powder (for example, freeze-dried powder) that may be dissolved in physiological saline or the like prior to use.

Another embodiment of the present disclosure relates to a method for killing proliferative cells, this method comprises contacting these cells with the isolated vaccine composition of the present disclosure.

Another embodiment of the present disclosure relates to the treatment of cancer patients, comprising administering an effective amount of the vaccine composition of the present disclosure.

In certain aspects of the present disclosure, cells may be contained in a patient, and these cells may be proliferative cells, neoplastic cells, precancerous cells, or metastatic cells. The administration may be oral administration, intraperitoneal administration, intravenous administration, intraarterial administration, intramuscular administration, intradermal administration, subcutaneous administration, transdermal administration, nasal administration, or transrectal administration. In certain aspects, the composition is administered via systemic administration, especially via intravascular administration (including modes of administration such as injection and perfusion).

In one embodiment of the present disclosure, molecular cloning and vector construction methods are well known in the art, and any one of such methods may be used to generate constructs to provide elements such as double-strand break-inducing enzymes, artificial target sites, targeting vectors, cell proliferation factors or any other useful element. Vector construction is performed using standard molecular biology techniques. Any transformation method may be used, and vector construction and/or insert preparation may be modified accordingly.

In another embodiment of the present disclosure, the amino acid sequence of the heterologous antigen may be inserted into any site of the amino acid sequence of the wild-type Listeriolysin O (LLO) polypeptide encoded by the sequence as set forth in SEQ ID NO:1. Alternatively, the amino acid sequence of the heterologous antigen of the present disclosure may be inserted before the amino acid at position 514, 515, 516, 517, 518, 519, 520, 521, 522, 523, 524, 525, 526, 527, 528, or 529 in the amino acid sequence of the wild-type Listeriolysin O (LLO) polypeptide encoded by the sequence as set forth in SEQ ID NO:1. In one example, the amino acid sequence of the heterologous antigen of the present disclosure may be inserted between the amino acid at position 523 and the amino acid at position 524 in the amino acid sequence of the Listeriolysin O (LLO) polypeptide encoded by the sequence as set forth in SEQ ID NO:1.

In another embodiment of the present disclosure, the amino acid sequence of the heterologous antigen may be inserted into any site of the amino acid sequence of the recombinant Listeriolysin O (LLO) polypeptide encoded by the sequence as set forth in SEQ ID NO: 3. In one example, the amino acid sequence of the amino acids at positions 533 and 534 in the amino acid sequence of the recombinant Listeriolysin O (LLO) polypeptide encoded by the sequence as set forth in SEQ ID NO:3 may be replaced by the amino acid sequence encoding the heterologous antigen of the present disclosure.

In another embodiment of the present disclosure, the heterologous antigen is chicken ovalbumin (OVA). In one embodiment, the fragment recombined into the LLO polypeptide has 2 amino acids to 40 amino acids in length. In another embodiment, the fragment recombined into the LLO polypeptide has 5 amino acids to 35 amino acids in length. In another embodiment, the fragment recombined into the LLO polypeptide has 8 amino acids to 28 amino acids in length. In one embodiment, the sequence of the OVA fragment recombined into the LLO polypeptide is $OVA_{248-275}$ (i.e., the $OVA_{28}$ in the present disclosure). In another embodiment, the sequence of the OVA fragment recombined into the LLO polypeptide is $OVA_{258-265}$ (i.e., the $OVA_{28}$ in the present disclosure).

In one example, the present disclosure further comprises a connecting peptide recombined into a vector (vaccine). In one example, the sequence of said connecting peptide is a $(G_4S)_2$ sequence linked to fusion protein. In another embodiment, said fusion protein is linked to a connecting peptide at both ends; alternatively, the sequence of said connecting peptide is $(G_4S)_2$ sequence.

EXAMPLES

Other objects, features and advantages of the present disclosure will become apparent from the following detailed description. However, it should be understood that the detailed description and specific Examples (although representing the specific embodiments of the present disclosure) are given for explanatory purposes only, since various changes and modifications made within the spirit and scope of the present disclosure will become apparent to those skilled in the art after reading this detailed description.

Unless explicitly and specifically stated to the contrary, in the embodiments involved in all Examples of the present disclosure, the insertion sites of OVA are all located between the amino acid at position 523 and the amino acid at position 524 in the amino acid sequence of the wild-type LLO polypeptide that is encoded by the sequence as set forth in SEQ ID NO:1.

Unless otherwise specified, all reagents and raw materials adopted in the present disclosure are commercially available.

The main reagents used in the present disclosure are as follows: Plasmid Mini Extraction Kit (AXYGEN), Gel Extraction Kit (AXYGEN), Q5 PCR high-fidelity DNA polymerase (NEB), T4 DNA ligase (NEB), Ezmax for One-Step Cloning Kit (tolo bio), Human IFN-γ ELISPOT Set (BD™, a trademark of "Becton, Dickinson and Company"), Mouse IFN-γ ELISPOT Set (BD™), electroporator (Bio-Rad)-, 1640 culture medium (Gibco), Mouse M-CSF (Miltenyi Biotec), anti-His-HRP (Genscript), WESTERN ECL Chromogenic reagent (BioRad).

Example 1: Construction of the Plasmid for an Attenuated *Listeria*

An attenuated *Listeria* was used as the vector strain to prepare the vaccine in the present disclosure. Illustratively, the strain used for preparing the vaccine in the present disclosure was Lm 10403SΔactA (the construction method of the aforementioned strain could be exemplarily referred to the following literature: Shen H et. al., PNAS, 92(9): 3987-91, 1995). This strain lacked the actA gene, so that the microbe that infected the host cell was unable to spread to neighboring cells via its unique actin tail, thereby greatly reducing its toxicity and pathogenicity. As compared with the wild-type strain Lm 10403S ($LD_{50}$ was $1\times10^4$ cfu), Lm-ΔactA had an $LD_{50}$ of $0.5\times10^8$ cfu to $1\times10^8$ cfu and was proved to be highly attenuated.

Meanwhile, this strain retained the complete ability to escape from the lysosome via LLO, enter the cytoplasm of the host cell and proliferate rapidly, and express the protein to activate the specific T cell immune response.

The basic structure of the plasmid used in the present disclosure to express the antigen gene was as follows.

(1) Basic sequence for maintaining the stable replication of the plasmid: illustratively, pAM401 was used as the basic sequence of the plasmid in the present disclosure.

(2) Promoter for the transcription of the antigen gene: illustratively, Phly (that is, the promoter of LLO on the virulence island of the chromosome of Lm) was used in the present disclosure.

(3) Signal peptide sequence for expressing and secreting the antigen protein outside of *Listeria*: illustratively, the signal peptide sequence of LLO, such as the sequence as set forth in $LLO_{1-28}$ and $LLO_{22-529}$, was used in the present disclosure, so as to increase the expression level of the heterologous protein.

(4) *Listeria* belonged to prokaryotic cells, however, it was generally required that the antigen peptide used in a tumor vaccine was derived from an eukaryotic cell, therefore, the corresponding codon optimization was required to enable the expression of a protein of an eukaryotic cell in a prokaryotic cell. Illustratively, an optimized sequence as set forth in SEQ ID NO: 6 was used in the present disclosure.

(5) Tag sequence for detecting the secretory protein: illustratively, His tag or Flag tag was used as the tag sequence in the present disclosure.

(6) Restriction site used for the insertion of the antigen peptide: illustratively, PstI was used as the restriction site in the present disclosure.

Illustratively, the method for constructing the plasmid pAM401-Phly-$LLO_{1-28}$-BamHI-$LLO_{22-523}$-PstI-$LLO_{524-529}$-His in the present disclosure was as follows. Based on the plasmid pAM401-Phly-$LLO_{1-28}$-BamHI and using BamHI as the restriction site, BamHI-$LLO_{22-529}$-His-BamHI sequence obtained by gene synthesis was constructed to this vector via enzyme digestion and enzyme ligation method to obtain pAM401-Phly-$LLO_{1-28}$-BamHI-$LLO_{22-529}$-His-BamHI. In order to add an insertion site for the exogenous gene, the upstream and downstream primers were designed at the selected site (i.e., $LLO_{523-524}$), and the PstI restriction site was inserted between $LLO_{523}$ and $LLO_{524}$ via PCR reaction.

The schematic diagram of the structure of the plasmid that was constructed by the above-mentioned method and used to express the antigen gene was as shown in FIG. 1.

Example 2: Construction of the Plasmid for an Attenuated *Listeria* Used for Vaccine The construction of the plasmid for an *Listeria*-based vaccine required the insertion of the antigen gene into a plasmid vector on which a restriction site had been designed, and the gene sequence of the target antigen was synthesized after the gene codon optimization was carried out by the company.

Alternatively, the codon optimization process of $OVA_{28}$ was as follows.

the nucleotide sequence of mouse $OVA_{28}$ before the optimization of the corresponding codons (SEQ ID NO:5):

```
GATGAAGTCTCAGGCCTTGAGCAGCTTGAGAGTATAATCAACTTTGAAAA

ACTGACTGAATGGACCAGTTCTAATGTTATGGAA
```

the nucleotide sequence of $OVA_{28}$ after the optimization of the corresponding codons (SEQ ID NO:6):

```
GATGAAGTGAGCGGCCTGGAGCAGCTGGAGAGCATTATCAACTTCGAAA
AACTGACCGAGTGGACCAGCAGCAATGTGATGGAA
```

The product was cloned to the PstI site on pAM401-Phly-$LLO_{1-28}$-BamHI-$LLO_{22-523}$-PstI-$LLO_{524-540}$-His vector (simply referred to as PstI vector plasmid) by using the homologous recombination technology based on certain homologous sequences, the homologous sequences thereof were 5'-end homologous sequence (CCGAAATATAGTAATAAACTGCAG, SEQ ID NO:8) and 3'-end homologous sequence (CTGCAGGTAGATAATCCAATCGAA, SEQ ID NO:9).

The main steps were as follows.

20-μl PstI single restriction enzyme digestion system comprising PstI vector plasmid.

| | |
|---|---|
| PstI vector plasmid | 2 μg |
| PstI restriction enzyme | 2 μl |
| 10x NEB buffer solution 3.1 | 2 μl |
| deionized water | added until the total volume of the system reached 20 μl |

The reactants were reacted for 10 min to 30 min in a water bath at 37° C.

The digested products were subjected to DNA extraction and purification, that is, the PstI vector was digested and linearized.

A 20-μl homologous recombination system comprised the following components (1) to (5):

(1) digested and linearized PstI vector (2) exogenous PCR fragment comprising homologous sequences at both ends (3) 5× buffer solution: 4 μl (4) reaction enzyme: 2 μl (5) $ddH_2O$: added until the total volume of the system reached 20 μl After the system was kept in a water bath at 37° C. for 30 minutes, *E. coli* competent cells were transformed and spread on a resistant plate, and a single clone was selected for sequencing and verification.

Example 3: Preparation of an Attenuated *Listeria* Carrying the Plasmid of a Non-Integrative Antigen Peptide and a Vaccine Comprising the Aforementioned Strain The plasmid for the attenuated *Listeria* used for the vaccine that was verified as correct by sequencing was transformed into an attenuated *Listeria* strain by electrotransformation technology, and a single clone was selected for the subsequent verification of the expression of the plasmid.

The specific steps of the above-mentioned electrotransformation were as follows.

(1) Preparation of electro-transformation competent cells (i) *Listeria* cultured overnight was transferred into 100 to 250 ml of brain-heart infusion broth (BHI) medium at a ratio of 1:50 to 1:200 and was subjected to shaking culture at 37° C. until the $OD_{600}$ value reached 0.2 to 0.25.

(ii) Penicillin (PNG) was added thereto until the final concentration was 10 μg/ml, and the cultivation was continued for about two hours until the OD value reached 0.3 to 0.9;

(iii) The mixture was subjected to high-speed centrifugation at 4° C. for 5 to 10 minutes to collect the microbes.

(iv) The microbes were re-suspended with 200 ml of 10% glycerin and washed twice.

(v) The microbes were re-suspended with 45 ml of 10% glycerin and a sterile solution of lysozyme was added thereto until the final concentration was 10 μg/ml. The resulting mixture was kept at ambient temperature for 20 minutes and mixed evenly by making it upside down every 10 minutes.

(vi) The mixture was subjected to high-speed centrifugation at 4° C. for 10 minutes to collect microbes, and then the microbes were washed once with 20 ml of 10% glycerin.

(vii) The microbes were re-suspended with 1 ml of 10% glycerin, dispensed into separate tubes (50 μl/tube), and stored at −80° C.

(2) Determination of the most suitable electrotransformation conditions (i) One tube of competent cells were taken, thawed, and placed on ice.

(ii) 1 μg of the plasmid to be transformed was added into the competent cells and the mixture was mixed evenly.

(iii) The above-mentioned mixed system was added into a pre-cooled electroporating cup (1 mm) and subjected to electric shock treatment. The conditions of the electric shock treatment were as follows. The electric field strength was 10 kV/cm, the resistance was 200Ω, the capacitance was 25 μF, and the electric shock treatment lasted for 5 to 6 ms.

(iv) The resulting mixture was re-suspended with BHI medium and left to stand at ambient temperature for 1 hour.

(v) The microbes were spread on a resistant plate added with BHI and cultured overnight at 37° C. by placing the plate upside down, and a single colony was picked for verification.

The verified strains/colonies could be used as an attenuated *Listeria*-based vaccine.

Example 4: Improvement and Detection of the Expression of the Heterologous Protein by the Attenuated *Listeria*

*Listeria* was cultured overnight in BHI liquid medium at ambient temperature, the microbes were removed by centrifugation, a solution of TCA (trichloroacetic acid)/acetone was added to the supernatant, and the mixture was precipitated under a condition of −20° C. The precipitated protein was collected by ultra-high-speed centrifugation and washed twice with acetone to remove the residual TCA. A protein loading buffer containing 0.01 N NaOH was used to dissolve the precipitate. The sample was loaded after the protein was boiled and denatured, and a Western blot assay was conducted to determine the expression level of the protein via the tag attached to the protein. In one embodiment, the aforementioned tag may be selected from Flag tag or His tag.

Example 5: Culture of Primary BMDMs

Female 8-week-old C57 mice were sacrificed by $CO_2$ asphyxiation and cervical dislocation. The femoral neck was incised and placed in 75% alcohol in an ice bath, and transferred into PBS on a clean bench. The muscle layer was isolated with sterilized surgical forceps and surgical scissors, and the femoral neck was transferred to 1640 complete culture medium. The femoral heads at both ends were cut open by a surgical scissor, 1640 complete culture medium was sucked by using a syringe and was used to flush the bone cavity until it became white. The 1640 complete culture medium containing cells were filtered through a mesh, the red blood cells were lysed by red blood cell lysis solution, and then cells were collected by centrifugation at 1000 rpm. Cells were re-suspended in 1640 complete culture medium containing 10 ng/μl of GM-CSF cytokine. Cells were cultured in an amount enough for each mouse to be inoculated with all the cells cultured on one 6-well plate. Afterwards, the culture medium was replaced on Day 4, and a large amount of BMDMs (bone marrow-derived macrophages) could be harvested on Day 6 or Day 7 and could be used in the experiments.

Example 6: Treating BMDMs with an Attenuated *Listeria* Carrying the Plasmid of a Non-Integrative Antigen Peptide BMDMs cultured up to Day 6 or Day 7 were washed twice with PBS, and 1640 complete culture medium (free of any antibiotics) containing the attenuated *Listeria* obtained in Example 3 was added therein. Cells were treated in a cell incubator for 30 min and immediately washed three times with PBS. The culture medium was then replaced with a 1640 complete culture medium containing 5 ng/μl of gentamicin and the extracellular attenuated *Listeria* was treated with the 1640 complete culture medium containing 5 ng/μl of gentamicin for 1 h. The resulting cells could be used in the experiment.

Example 7: Acquisition of C57 Mice Bone Marrow-Derived Macrophages

BMDMs derived from female 8-week-old C57 mice were subjected to primary culture. Red blood cells in bone marrow were lysed and filtered. After centrifugation and cell collection, cells were re-suspended in 1640 complete culture medium containing GM-CSF cytokine and then seeded in 6-well plates for cultivation. Observation was carried out under an inverted phase contrast microscope on Day 4.

Figure 2:
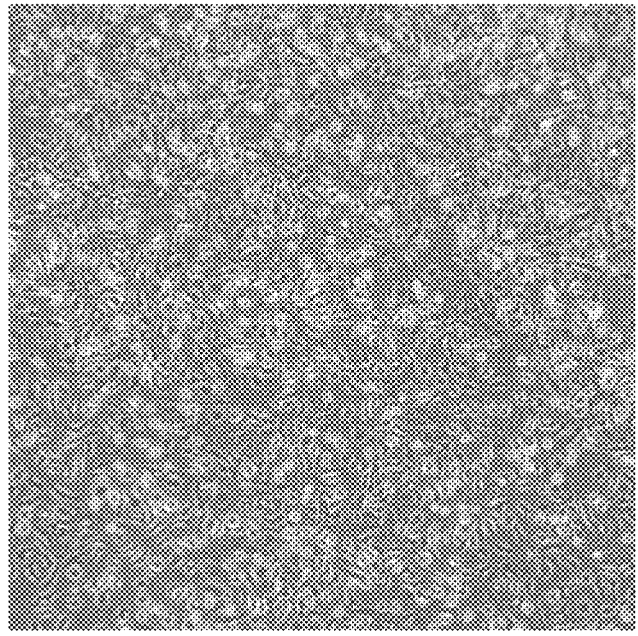
FIG. 2 shows the observation results of cell morphology under an ordinary inverted phase contrast microscope (100×) on Day 4 of the primary culture of BMDMs.

The experimental results were as shown in FIG. 2. It was found that some adherent cells were polygonal and these cells were C57 mice bone marrow-derived macrophages, which were cultured to Day 6 or Day 7 and then used in the experiment.

Example 8: Screening the Expression Level of Strains by Dot ELISA Assay

In order to prepare LM-LLO540 vaccine and LM-LLO540-OVA28 vaccine for use in subsequent cell therapy and obtain LM-LLO540 and LM-LLO540-OVA28 strains with high expression level, the inventors cultivated different single colonies of LM-LLO540 and LM-LLO540-OVA28, allowed the protein in the supernatant to be precipitated, and conducted a preliminary screening by Dot ELISA assay.

The specific steps of the above-mentioned preliminary screening were as follows. Single colonies (Colony 1 and Colony 2) on LM-LLO540 plate and single colonies (Colony 1 to Colony 6) on LM-LLO540-OVA28 plate were respectively picked, added to BHI culture medium containing chloramphenicol, and subjected to shaking culture in a shaker for 8 h to 30 h. The resultant was subjected to centrifugation to collect the microbes. 1 ml of supernatant was taken and mixed evenly with a TCA/acetone solution of which the volume was three times the volume of the supernatant, and the resultant was allowed to precipitate overnight. The precipitated protein was collected by centrifugation at 15000 rpm, and washed twice with acetone precooled with ice to remove the remaining TCA. Excess acetone was volatilized in a fuming cupboard, and a protein loading buffer was used to dissolve the precipitate. After being boiled and denatured, the sample was spotted on an NC membrane and was washed three times with TBST after air-drying. The membrane was blocked with TBST containing 5% skim milk for 1 h and washed three times with TBST. The membrane was incubated with HRP-labeled Anti-His antibody at room temperature for 1.5 h or at 4° C. overnight, and washed three times with TBST. ECL Chromogenic reagent was added dropwise on the NC membrane, and a Bio-Rad gel imager was used for development.

Figure 3:
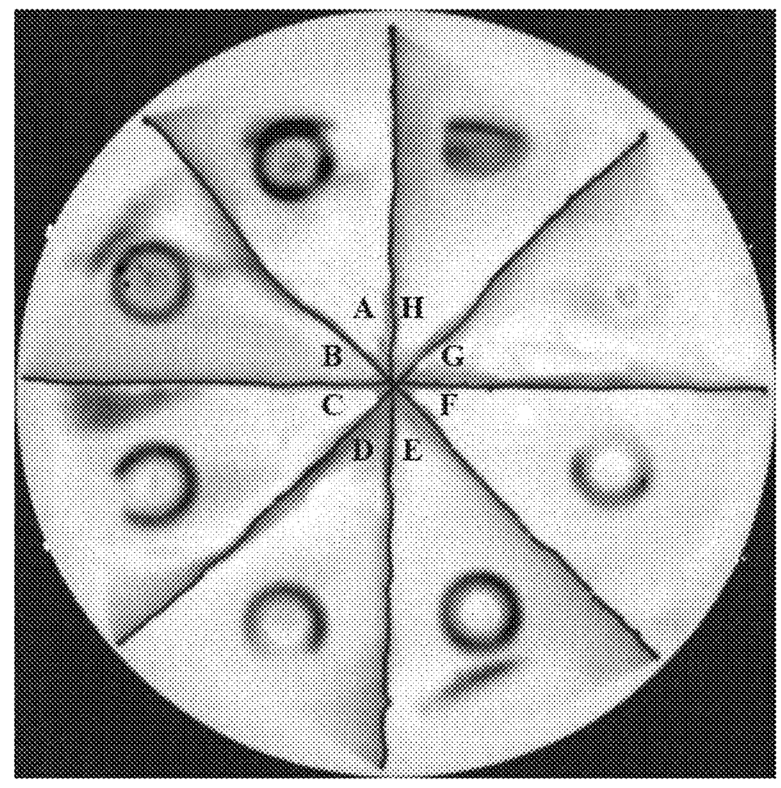
FIG. 3 shows the screening results of attenuated *Listeria* with high expression of target protein by Dotplot. Sections A to F: LM 10403SΔactA (pAM401-Phly-$LLO_{1-28}$-$LLO_{22-523}$-$(G4S)_2$-$OVA_{28}$-$(G4S)_2$-$LLO_{524-529}$-His) simply referred to as LM-LLO540-OVA28, i.e., 1 ml of the concentrated sample of the precipitated protein in the supernatant of colonies 1 to 6 on the plate; Sections G and H: LM 10403SΔactA (pAM401-Phly-$LLO_{1-28}$-$LLO_{22-267}$-PstI-$LLO_{524-529}$-His) simply referred to as LM-LLO540, i.e., 1 ml of the concentrated sample of the precipitated protein in the supernatant of colonies 1 to 2 on the plate.

The experimental results were as shown in FIG. 3. The experimental results indicated that Colony 1 and Colony 5 of LM-LLO540-OVA28 had relatively high expression level. Therefore, Colony 1 and Colony 2 of LM-LLO and Colony 1 and Colony 5 of LM-LLO540-OVA28 were then picked to conduct western blot assay, so as to further reflect the expression level accurately.

Example 9: Verification of the Expression Level of the Strains by Western Blot Assay The inventors conducted Western blot assay so as to further determine the expression level of Colony 1 and Colony 2 of LM-LLO and Colony 1 and Colony 5 of LM-LLO540-OVA28. The specific procedure was as follows. Single colonies (Colony 1 and Colony 2) on LM-LLO540 plate and single colonies (Colony 1 and Colony 5) on LM-LLO540-OVA28 plate were respectively picked, added to a BHI culture medium containing chloramphenicol, and subjected to culture in a shaker for 8 h to 30 h. The resultant was then subjected to centrifugation at 4500 rpm to precipitate the microbes. 10 ml of supernatant was taken and mixed evenly with a TCA/acetone solution, and the resultant was allowed to precipitate overnight. The precipitated protein was collected by centrifugation at 15000 rpm, and washed twice with precooled acetone to remove the remaining TCA. Excess acetone was volatilized in a fuming cupboard, and a protein loading buffer was used to dissolve the precipitate, which was stored after being boiled and denatured.

10% separation gel and 4% stacking gel were formulated respectively. 20 μl of the sample was loaded to each well and subjected to an electrophoresis at 80 V, and the voltage was changed to 120 V when the sample reached the junction of the stacking gel and the separation gel. After the electrophoresis was completed, the separation gel was taken, the filter paper and a 0.22-μm PVDF membrane (pre-activated in methanol) were cut to the same size as the gel, and the transfer membrane was placed in an ice bath. The membrane was blocked with TBST containing 5% skim milk and washed three times with TBST. The membrane was incubated with HRP-labeled Anti-His antibody at room temperature and washed three times with TBST. ECL Chromogenic reagent was added dropwise on the PVDF membrane, and a Bio-Rad gel imager was used for development.

Figure 4:
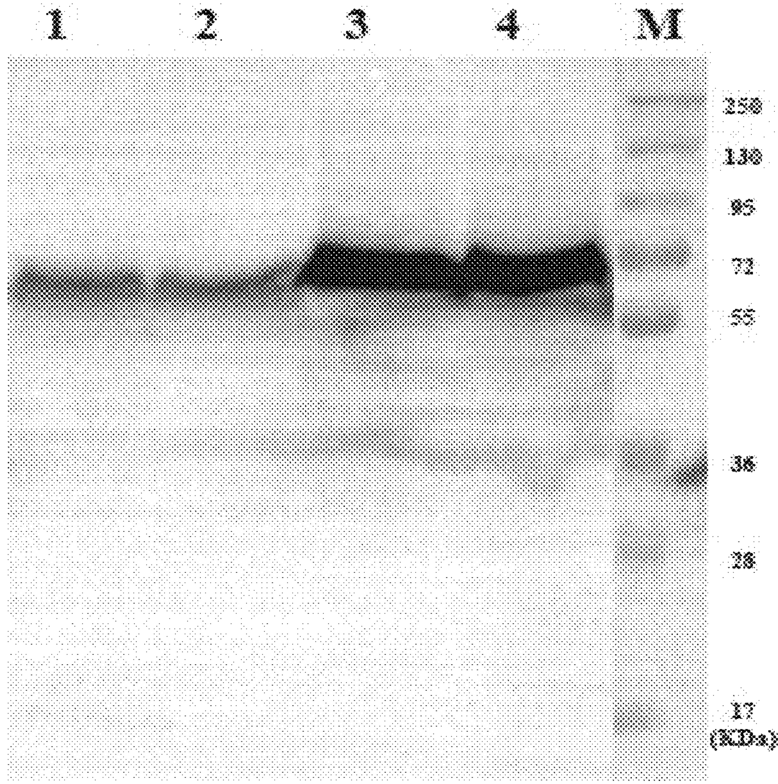
FIG. 4 shows the expression results of attenuated *Listeria* detected by Western blot. M: 250 KDa protein ladder as standard reference, Lanes 1 and 2: LM-LLO540, i.e., the concentrated sample of the precipitated protein in the supernatant of colonies 1 and 2 on the plate; Lanes 3 and 4: LM-LLO540-OVA28, i.e., the concentrated sample of the precipitated protein in the supernatant of colonies 1 and 5 on the plate.

The experimental results were as shown in FIG. 4. The experimental results indicated that Colony 1 and Colony 5 of LM-LLO540-OVA28 showed good expression level. Therefore, Colony 1 and Colony 2 of LM-LLO and Colony 1 and Colony 5 of LM-LLO540-OVA28 were respectively prepared into *Listeria* vaccines, which were stored after counting and sub-packaging.

Example 10: BMDMs Treated with an LM Vaccine Expressing an Antigen Peptide could be Used for Antigen Presentation An OVA model was utilized and BMDMs treated with LM-LLO540-OVA28 and OT1 $CD8^+$ T cells were co-cultured in an ELISPOT well plate. If the treated BMDMs showed sign of antigen presentation, OT1 $CD8^+$ T cells would be activated to secrete IFN-γ interferon, further resulting in the appearance of spots in ELISPOT assay.

The specific process of the experiment was as follows. LM-LLO was set as the experimental control group, a group where the treated BMDMs and OT1 $CD8^+$ T cells were co-cultured (containing 10 ng/μl of OVA polypeptide) was set as the positive control group, and a group where untreated BMDMs and OT1 $CD8^+$ T cells were co-cultured was set as the negative control group. The specific process was as follows. BMDMs cultured to Day 7 were washed twice with PBS. BMDMs were respectively treated with 1640 complete culture medium, then washed three times with PBS, and cultured after replacing the medium with 1640 complete culture medium. The spleen of OT1 mouse was incised, grinded and then allowed to pass a sieve. The collected cells were stained with CD8-PE dye and washed twice with PBS. The collected cells and anti-PE magnetic beads were co-incubated on ice. The cells were collected by centrifugation and then allowed to pass a magnetic column, and cells bound to anti-PE magnetic beads were adsorbed on the magnetic column. Subsequently, the magnetic column was removed from the magnetic stand to collect the target cells, i.e., OT1 $CD8^+$ T cells. After centrifugation and counting, BMDMs treated under different conditions and $CD8^+$ T cells were co-cultured in an ELISPOT well plate to conduct ELISPOT assay (for specific protocol of ELISPOT assay, please refer to the specification of BD™ ELISPOT Mouse IFN-γ ELISPOT Set, product number: 551083).

Figures 5, 6:
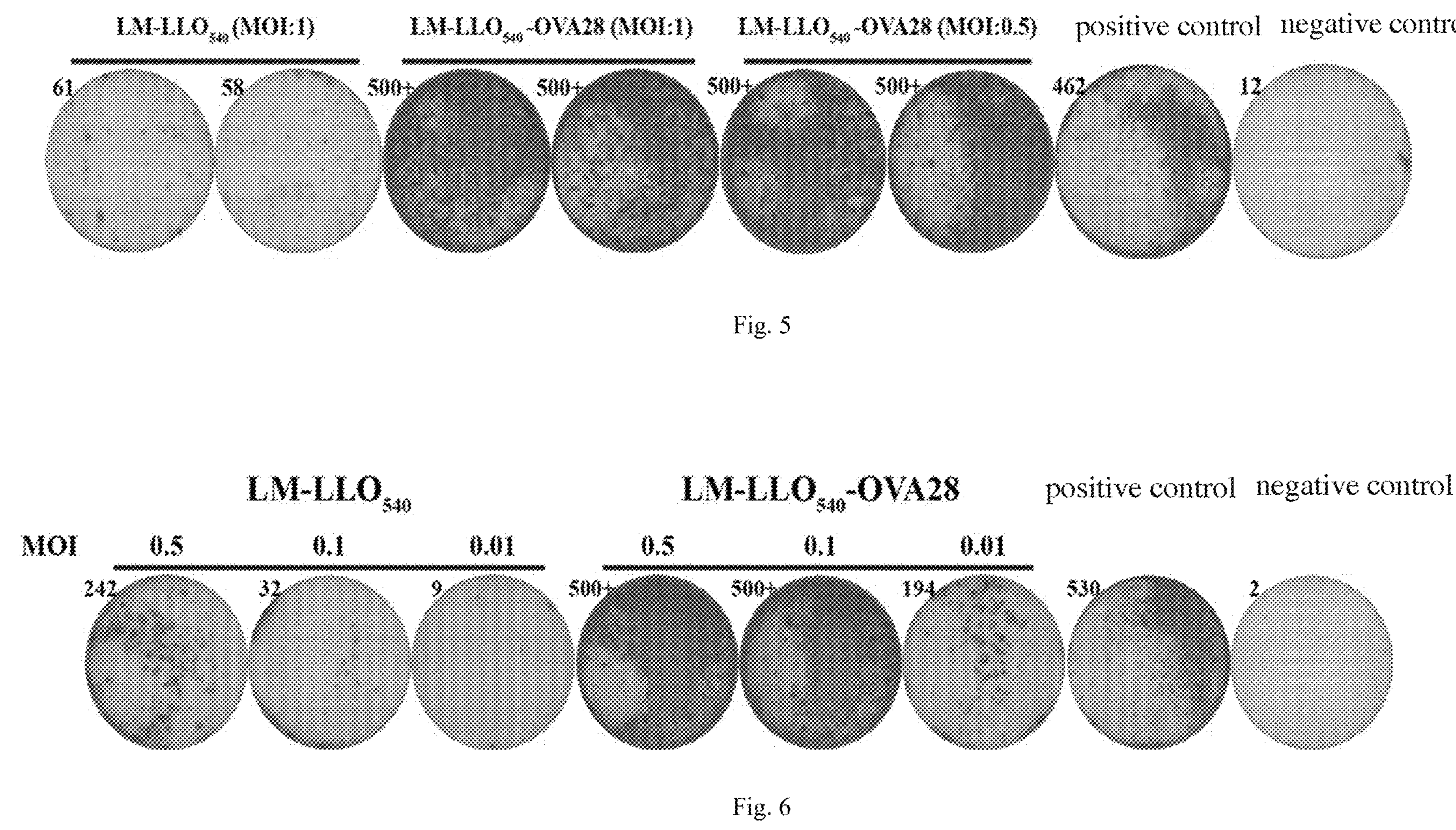
FIG. 5 shows the schematic diagram of the results of antigen presentation detected by ELISPOT in vitro after treating BMDMs with the attenuated *Listeria* for 24 h.
FIG. 6 shows the schematic diagram of the results of antigen presentation detected by ELISPOT in vitro after treating BMDMs with the attenuated *Listeria* for 8 h.
Figure 7A:
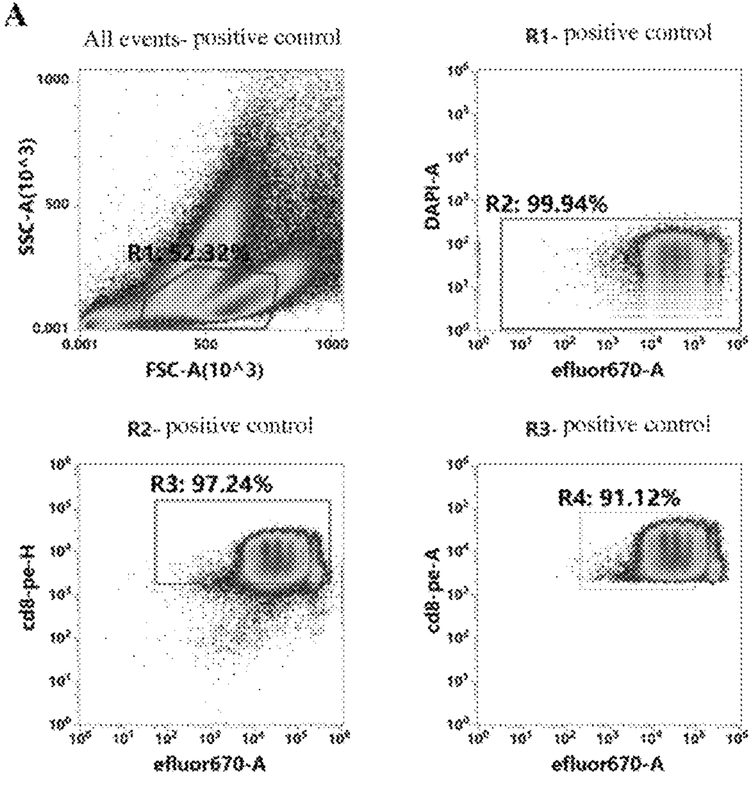
FIG. 7A to FIG. 7H show the schematic diagram of the in-vitro test results of the influence of BMDMs treated with the attenuated *Listeria* on the proliferation of T cells. Among them.
Figure 7B:
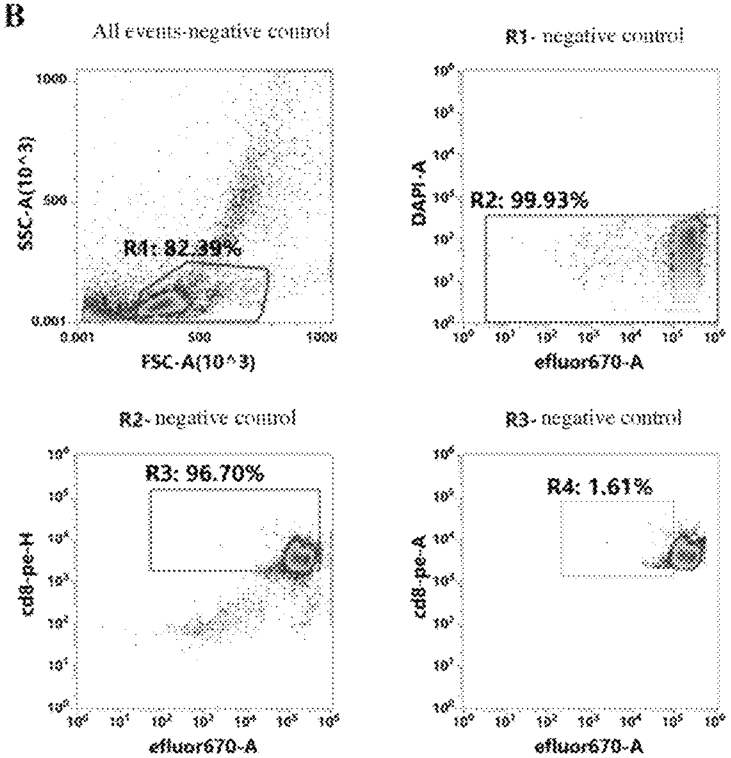
Figure 7C:
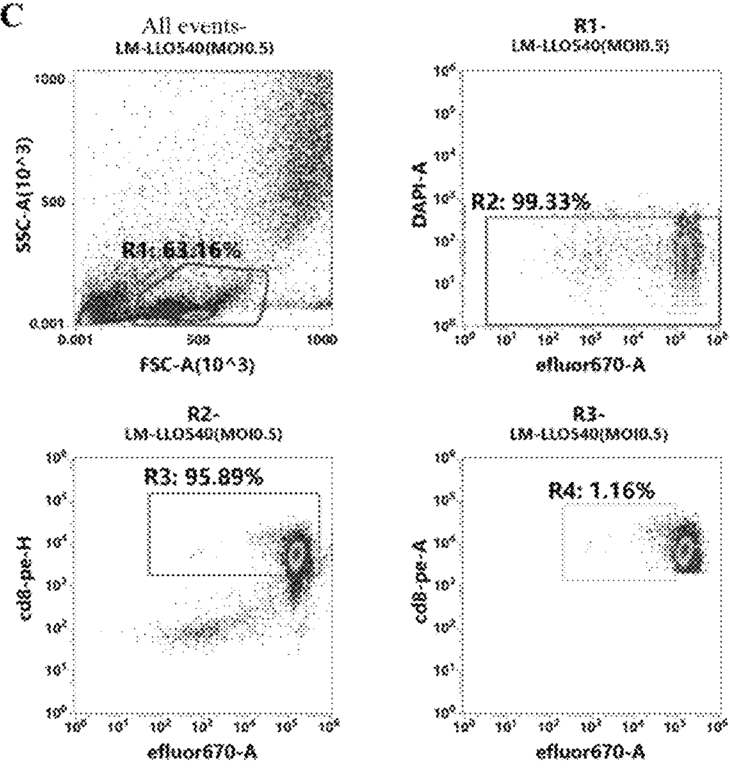
Figure 7D:
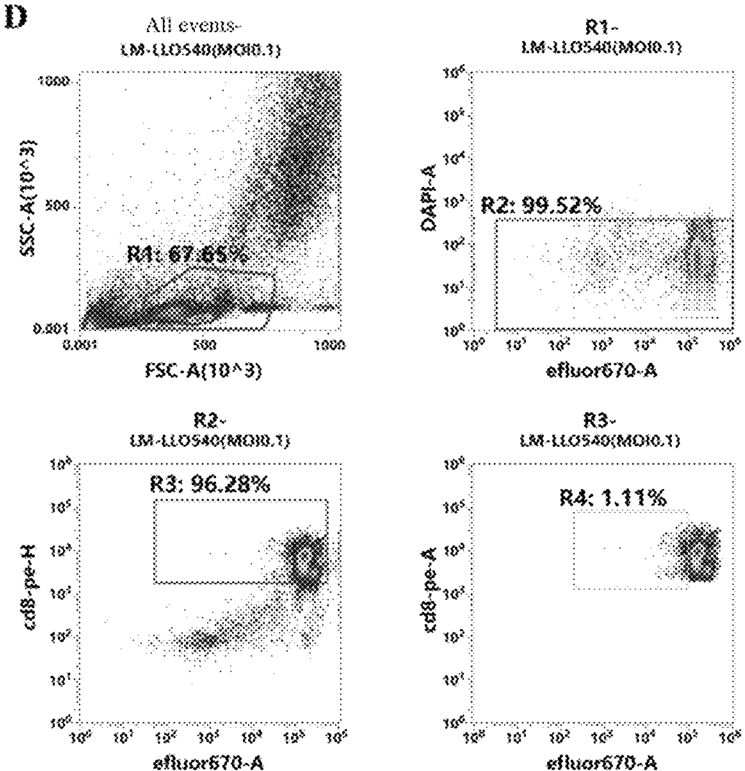
Figure 7E:
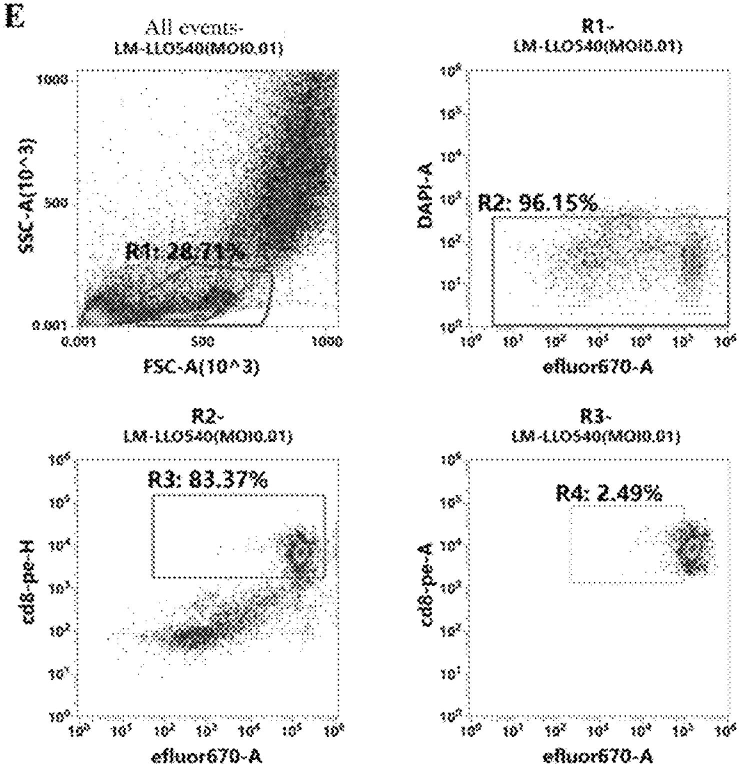
Figure 7F:
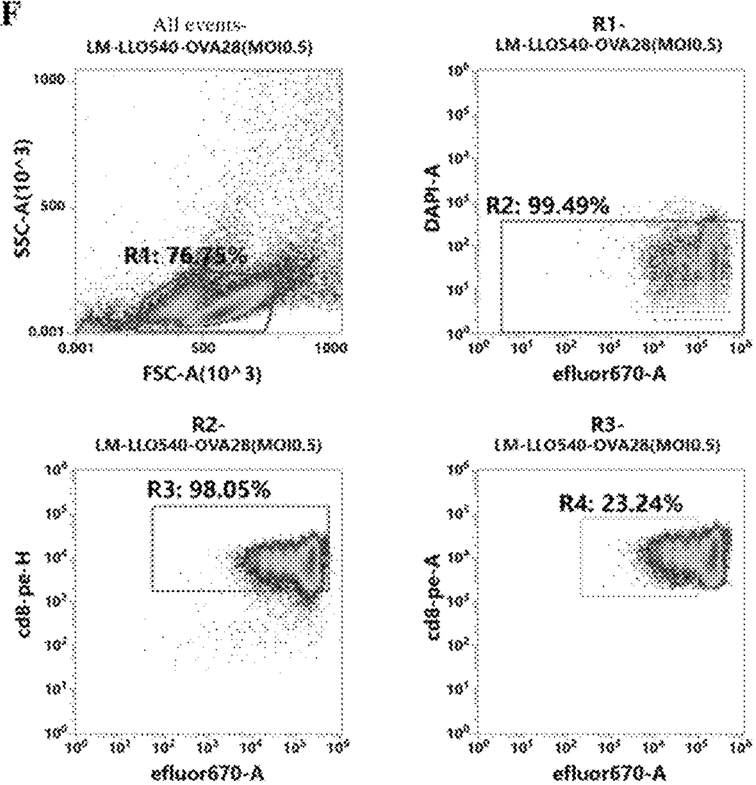
Figure 7G:
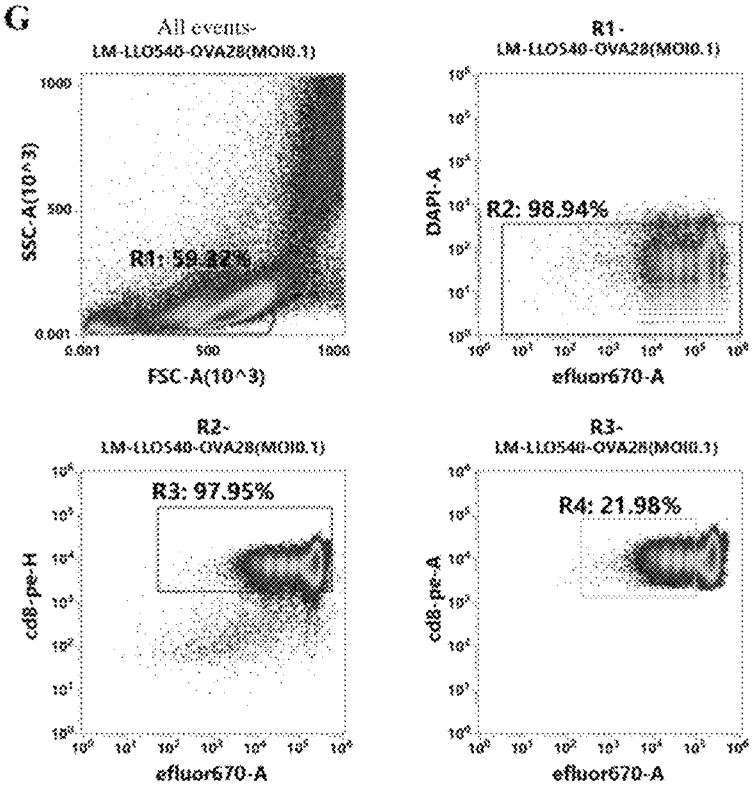
Figure 7H:
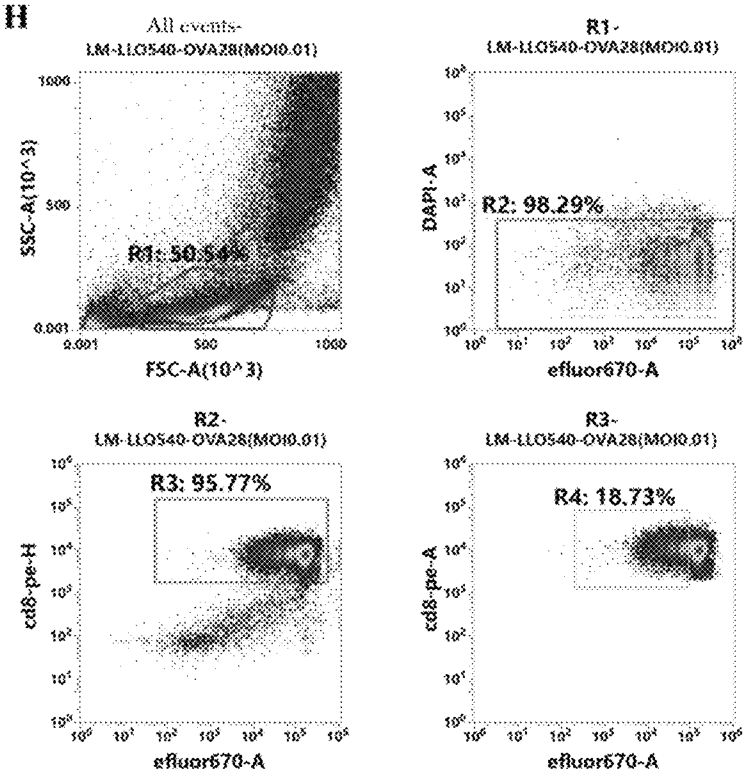

The experimental results were as shown in FIG. 5. The experimental results indicated that obvious and strong ELISPOT response appeared in experimental groups (LM-LLO540-OVA28 (MOI: 1, MOI: 0.5) groups) while no obvious ELISPOT response appeared in the experimental control group (LM-LLO540 (MOI: 1) group), thus proving in vitro that treating BMDMs with LM-LLO540-OVA28 was capable of activating BMDMs, enabling OVA28-specific antigen presentation by these BMDMs, and thus activating OT1 $CD8^+$ T cells to secrete IFN-γ interferon. Such experimental results provided direct evidence for the anti-tumor immune response in vivo.

Example 11: Optimization of the Conditions Under which BMDMs were Treated with an LM Vaccine Expressing an Antigen Peptide This experiment aimed at verifying in vitro that the response time of antigen presentation could be shortened by carefully selecting the MOI infection coefficient upon treating BMDMs with an LM vaccine expressing an antigen peptide.

The specific process of the experiment was as follows. BMDMs cultured to Day 7 were washed twice with PBS. BMDMs were respectively treated with 1640 complete culture medium, then washed three times with PBS, and cultured after replacing the medium with 1640 complete culture medium. The spleen of OT1 mouse was incised, grinded and then allowed to pass a sieve. The collected cells were stained with CD8-PE dye, placed on ice, and washed twice with PBS. The collected cells and anti-PE magnetic beads were co-incubated on ice. The cells were collected by centrifugation and then allowed to pass a magnetic column, and cells bound to anti-PE magnetic beads were adsorbed on the magnetic column. Subsequently, the magnetic column was removed from the magnetic stand to collect the target cells, i.e., OT1 $CD8^+$ T cells. After centrifugation and counting, BMDMs treated under different conditions (cultured for 8 h after the treatment) and $CD8^+$ T cells were co-cultured in an ELISPOT well plate to conduct ELISPOT assay (for specific protocol of ELISPOT assay, please refer to the specification of BD™ ELISPOT Mouse IFN-γ ELISPOT Set, product number: 551083).

The experimental results were as shown in FIG. 6. The experimental results indicated that obvious and strong ELISPOT response appeared in experimental groups (LM-LLO540-OVA28 (MOI: 0.5, MOI: 0.1, MOI: 0.01) groups), thus proving in vitro that treating BMDMs with LM-LLO540-OVA28 at an MOI as low as 0.01 was still capable of activating BMDMs, enabling OVA28-specific antigen presentation by these BMDMs, and thus activating OT1 $CD8^+$ T cells to secrete IFN-γ interferon. Such experimental results sufficiently proved the in-vitro effectiveness of the method of the present disclosure and proved that the method of the present disclosure was capable of further improving the in-vitro safety of using an attenuated *Listeria*.

Example 12: Demonstration of the Activation of T Cells by the Treated BMDMs

The activation of T cells by the treated BMDMs was proved by determining the proliferation activity of the activated OT1 CD8+ T cells by flow cytometry.

The specific process of the experiment was as follows. BMDMs cultured to Day 7 were washed twice with PBS. BMDMs were respectively treated with 1640 complete culture medium (free of penicillin-streptomycin), then washed three times with PBS, and cultured after replacing the medium with 1640 complete culture medium. The spleen of OT1 mouse was incised, grinded and then allowed to pass a sieve. The collected cells were stained with CD8-PE dye, and washed twice with PBS. The collected cells and anti-PE magnetic beads were co-incubated on ice. The cells were collected by centrifugation and then allowed to pass a magnetic column, and cells bound to anti-PE magnetic beads were adsorbed on the magnetic column. Subsequently, the magnetic column was removed from the magnetic stand to collect the target cells, i.e., OT1 $CD8^+$ T cells. Afterwards, the cytoplasm of OT1 $CD8^+$ T cells was stained with efluor670 dye, incubated on ice and then washed twice with PBS. After centrifugation and counting, BMDMs treated under different conditions (cultured for 8 h after the treatment) and $CD8^+$ T cells were co-cultured in a 96-well round-bottom culture plate for three days and then subjected to determination by a flow cytometer.

The experimental results were as shown in FIG. 7A to FIG. 7H. The experimental results indicated that OT1 $CD8^+$ T cells in experimental groups (LM-LLO540-OVA28 (MOI: 0.5, MOI: 0.1, MOI: 0.01) groups) proliferated significantly, and progeny OT1 $CD8^+$ T cells proliferated in three experimental groups accounted for 23.24%, 21.98% and 18.73% of the overall OT1 $CD8^+$ T cells, respectively. It could be seen from the diagrams illustrating the density of fluorescence intensity that progeny cells in all three experimental groups proliferated to the fourth generation while there was no proliferation of OT1 $CD8^+$ T cells in the experimental control groups (LM-LLO540 (MOI: 0.5, MOI: 0.1, MOI: 0.01) groups).

It was proved by the experiment that, under in-vitro conditions, BMDMs treated with LM-LLO540-OVA28 (MOI: 0.5, MOI: 0.1, MOI: 0.01) were capable of activating OT1 $CD8^+$ T cells and thus triggering the proliferation of OT1 CD8+ T cells, which further proved the effectiveness of the method of the present disclosure in eliciting antitumor immune response.

Example 13: Influence of BMDMs Treated with LM for Different Time Periods on Antigen Presentation According to the experiment designed by the inventors, BMDMs were treated with LM-LLO540-OVA28 at an MOI of 0.5 for 0 min, 15 min, 30 min, 60 min and 90 min, and then immediately co-cultured with OT1 $CD8^+$ T cells obtained by enrichment in an ELISPOT well plate. Two cell gradients (BMDM cells: $CD8^+$ T cells=$2\times10^4$: $10\times10^4$; BMDM cells: CD8+ T cells=$4\times10^4$: $20\times10^4$) were designed at each time point, and each set of the experiment was conducted in triplicate. A group wherein untreated BMDMs and OT1 $CD8^+$ T cells were co-cultured (containing 10 ng/μl of OVA polypeptide) was set as the positive control group in the experiment. Co-culture was carried out for 14 h to 20 h to conduct ELISPOT assay (for specific protocol of ELISPOT assay, please refer to the specification of BD™ ELISPOT Mouse IFN-γ ELISPOT Set, product number: 551083).

Figure 8:
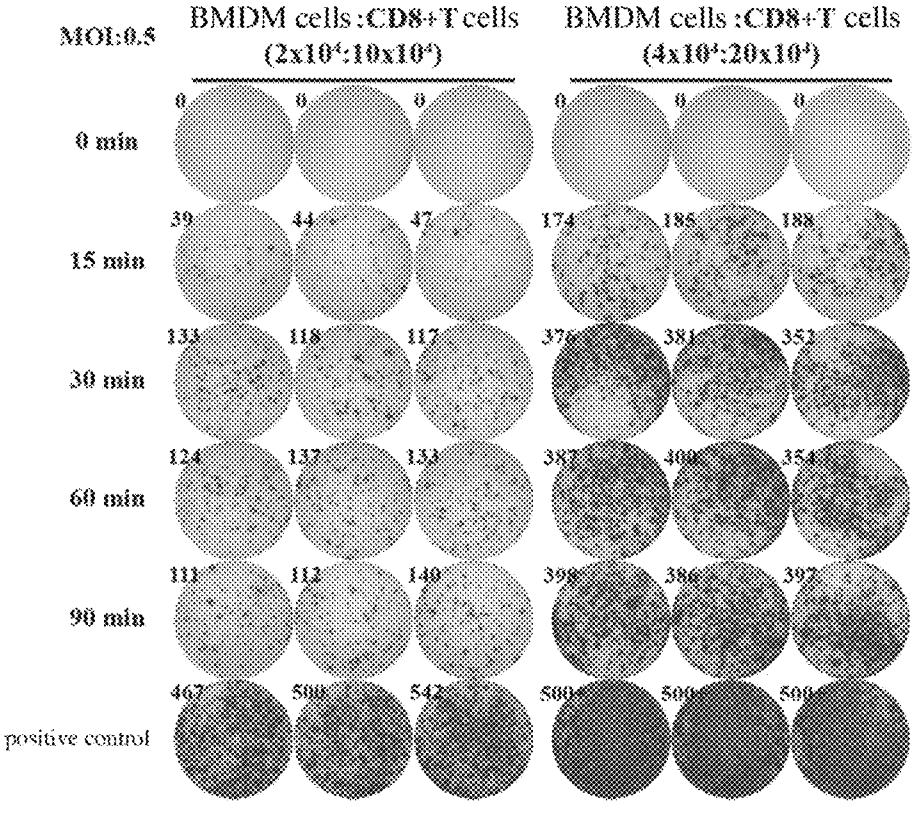
FIG. 8 shows the schematic diagram of the results of ELISPOT response upon treating BMDMs with LM-LLO540-OVA28 (MOI: 0.5) for different time periods.
Figure 9:
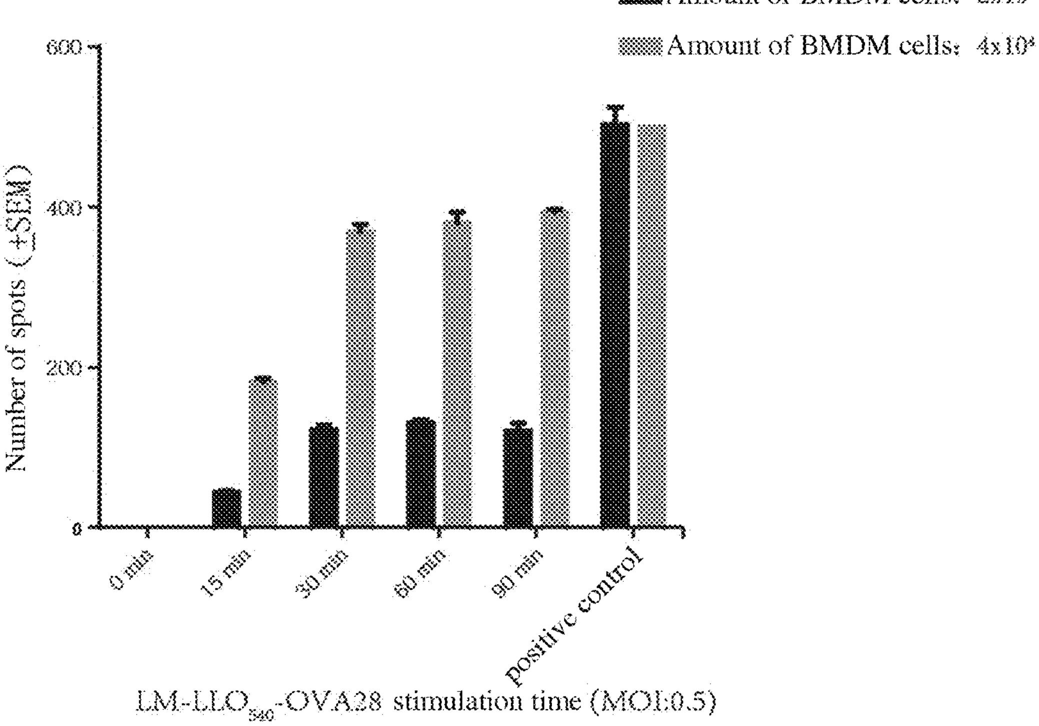
FIG. 9 shows the quantitative statistical histogram of ELISPOT spots of LM-LLO540-OVA28 with respect to the stimulation time.

The experimental results were as shown in FIG. 8 and FIG. 9. The experimental results indicated that upon treating BMDMs with LM-LLO540-OVA28 for a minimum of 15 min, LM-LLO540-OVA28 engulfed by BMDMs was sufficient to trigger a certain degree of antigen presentation, while treating BMDMs with LM-LLO540-OVA28 for 30 min, 60 min and 90 min was capable of causing strong ELISPOT response (as shown in FIG. 8). Meanwhile, there was little difference in the number of spots indicating ELISPOT response at three time points (i.e., 30 min, 60 min, 90 min) (as shown in FIG. 9), which indicated that it was only required to treat BMDMs with LM-LLO540-OVA28 (MOI: 0.5) for 30 min to maximize the OVA28-specific antigen presentation and demonstrated the simplicity and high efficiency of the steps of the present disclosure.

Example 14: Inoculating C57 Mice with EG7-OVA Cells, Treating the Mice Via Cell Therapy, and Determining the Antitumor Effects In order to further prove the effectiveness of this method in vivo, C57 mice were first inoculated subcutaneously with EG7-OVA cells to develop tumors and then treated via cell therapy, and the antitumor effects were determined. The inoculation amount of EG7-OVA cells was $2\times10^6$ cells, and tumor sizes were measured from the 6th day after inoculation. The tumor sizes of 20 mice were normalized and these mice were divided to four groups as below.

| Group A: 1 × $10^6$ BMDM control group |
|---|
| five mice in total, each injected with 1 × $10^6$ BMDMs/100 μl, simply referred to as control group |
| Group B: LM-LLO540-OVA28 (MOI 0.5)-treated BMDM experimental group |
| five mice in total, each injected with 1 × $10^6$ cells/100 μl, simply referred to as 1 × $10^6$ experimental group |

-continued

| Group C: LM-LLO540-OVA28 (MOI 0.5)-treated BMDM experimental group |
|---|
| five mice in total, each injected with 3 × $10^6$ cells/100 μl, simply referred to as 3 × $10^6$ experimental group |
| Group D: LM-LLO540-OVA28 (MOI 0.5)-treated BMDM experimental group |
| five mice in total, each injected with 6 × $10^6$ cells/100 μl, simply referred to as 6 × $10^6$ experimental group |

Cell injection was conducted on Day 8 in control group, 1×$10^6$ experimental group, 3×$10^6$ experimental group, and 6×$10^6$ experimental group, and the tumor sizes were tracked and measured continuously. Tumor sizes were tracked and measured for 25 days.

Figure 10:
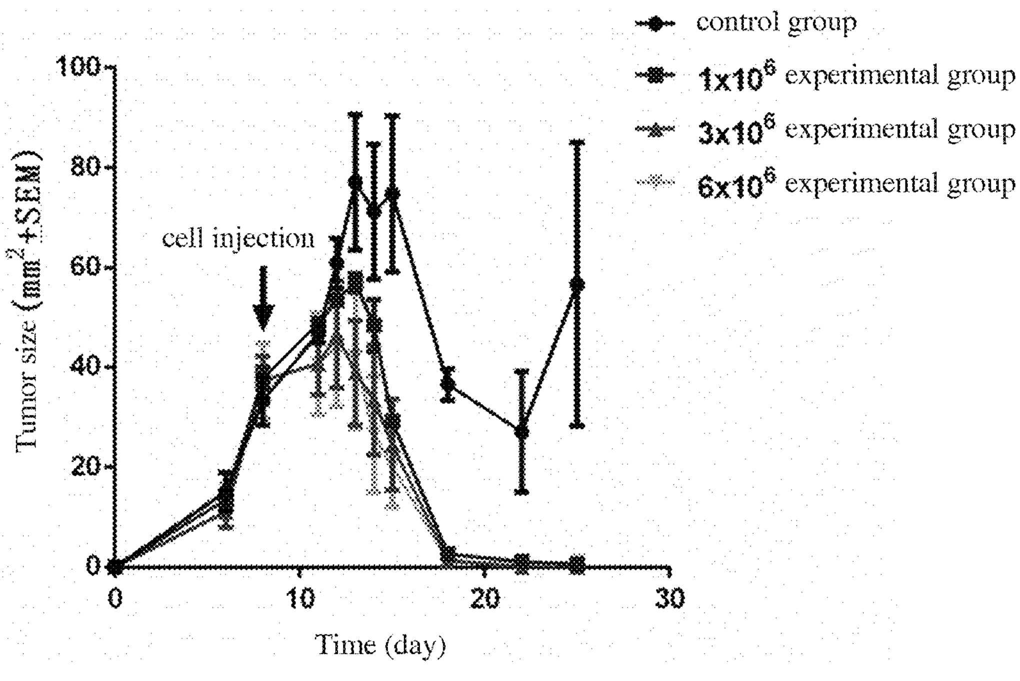
FIG. 10 shows the schematic diagram of the tumor growth curve of EG7 tumor model after the cell therapy.
Figure 11:
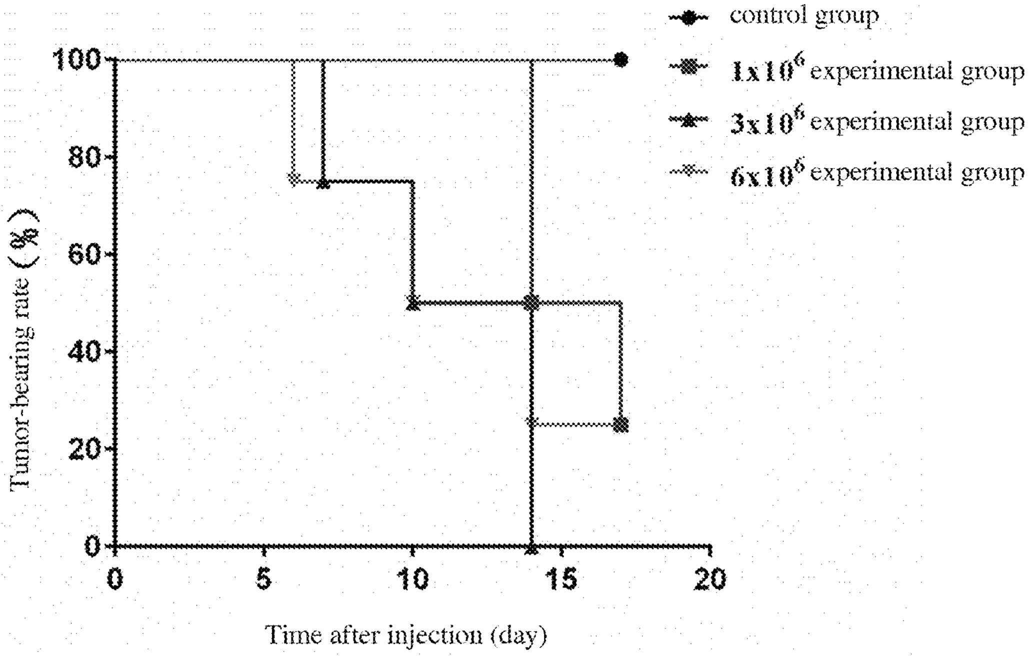
FIG. 11 shows the ladder diagram of the tumor-bearing rate among EG7 tumor models after the cell therapy.

The experimental results were as shown in FIG. 10 and FIG. 11. Among them, tumor growth curve was as shown in FIG. 10. It could be seen that, in 1×$10^6$ experimental group, 3×$10^6$ experimental group and 6×$10^6$ experimental group, a tendency of decrease in tumor size appeared successively from Day 12 to Day 15, and the tumors were basically eliminated till Day 18.

The statistical ladder diagram of the tumor-bearing rates among mice in each group was as shown in FIG. 11, which indicated that the tumor-bearing rates in 1×$10^6$ experimental group, 3×$10^6$ experimental group and 6×$10^6$ experimental group were significantly lower than that in control group. Such results demonstrated that this cell therapeutic method was capable of significantly reducing tumor size or eliminating tumor, thereby proving the feasibility of this method.

Example 15: Verification of the Activation of Tumor-Specific Immune Response by Cell Therapy in EG7 Tumor-Bearing Mouse Model Via ELISPOT Assay 3 to 7 drops of blood was drawn via tail vein on Day 24 after the cell injection in cell therapy and washed twice with PBS to obtain peripheral blood mononuclear cells, which were finally re-suspended in 100 μl of 1640 complete culture medium respectively and then added to a pretreated ELISPOT well plate. Subsequently, 10 ng/μl of OVA polypeptide was added to the ELISPOT well plate to stimulate the peripheral blood mononuclear cells to produce IFN-γ. Finally, the number of spots was quantified by enzyme-linked reaction to indicate the specific immune response to OVA polypeptide in each group (for specific protocol of ELISPOT assay, please refer to the specification of BD™ ELISPOT Mouse IFN-γ ELISPOT Set, product number: 551083).

Figure 12:
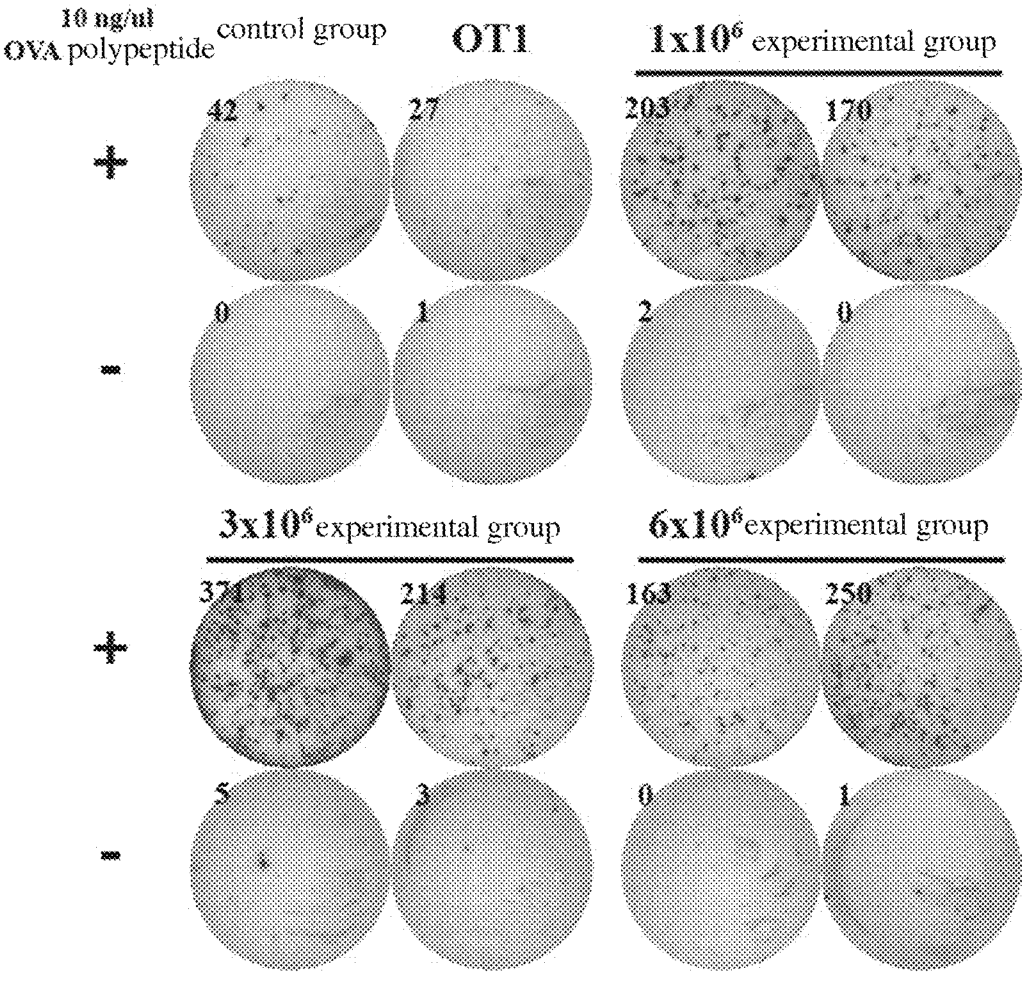
FIG. 12 shows the schematic diagram of the results of ELISPOT response 24 days after the cell therapy.

The experimental results were as shown in FIG. 12. According to the experimental results, there appeared relatively strong ELISPOT response in 1×$10^6$ experimental group, 3×$10^6$ experimental group and 6×$10^6$ experimental group, which indicated that OVA-specific immune response of the mouse immune system could be activated after the cell injection, thereby proving the effectiveness of the cell therapy of the present method.

Example 16: Determination of the Conditions for the Safe Use of an Attenuated *Listeria*

In order to further improve the safety of using an attenuated *Listeria*, LM-LLO540-OVA28 strain was first inactivated at 65° C. In order to verify the effect of inactivation, the strain was treated at 65° C. for 1 min or 5 min and then spread on a chloramphenicol-resistant plate, and the untreated LM-LLO540-OVA28 was set as control.

Figure 13:
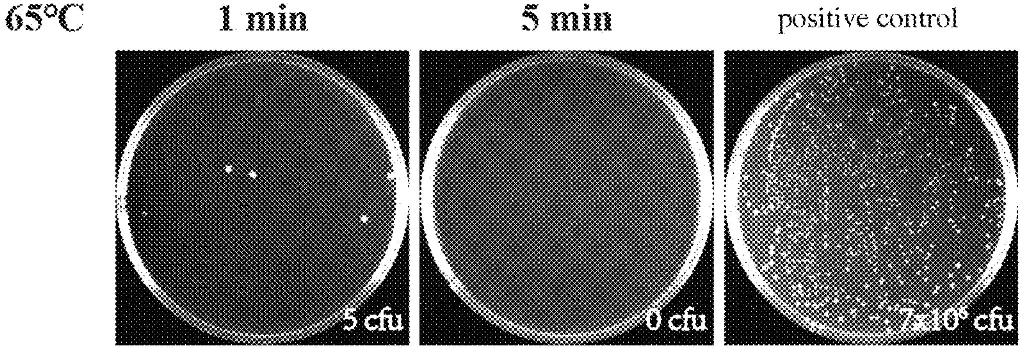
FIG. 13 shows the schematic diagram of the inactivation results of attenuated *Listeria* at 65° C.

The experimental results were as shown in FIG. 13. After being diluted and spread on the plate, the statistical result of LM-LLO540-OVA28 (not inactivated) was 7×$10^6$ cfu while the statistical results of LM-LLO540-OVA28 that had been treated at 65° C. for 1 min and 5 min were respectively 5 cfu and 0 cfu, indicating that treating LMs at 65° C. for 1 min was capable of inactivating 99% of LMs.

Example 17: Inoculating C57 Mice with EG7-OVA Cells, Treating the Mice Via Cell Therapy, and Determining the Antitumor Effects The experiment of cell therapy was conducted by using BMDMs treated with LM-LLO540-OVA28 (inactivated at 65° C. for 1 min) at an MOI of 0.5, and the effectiveness in eliciting antitumor response was determined. C57 mice were first inoculated subcutaneously with EG7-OVA cells to develop tumors and then treated via cell therapy, and the antitumor effects were determined. The inoculation amount of EG7-OVA cells was 2×$10^6$ cells, and tumor sizes were measured from the 6th day after inoculation. The tumor sizes of 20 mice were normalized and these mice were divided to four groups as below.

| Group A: PBS control group |
|---|
| five mice in total, each injected with 100 μl of PBS via tail vein, simply referred to as PBS control group |
| Group B: 1 × $10^6$ BMDM control group |
| five mice in total, each injected with 1 × $10^6$ BMDM/100 μl, simply referred to as BMDM control group |
| Group C: LM-LLO540-OVA28 (MOI 0.5)-treated BMDM experimental group |
| five mice in total, each injected with 1 × $10^6$ cells/100 μl, simply referred to as 1 × $10^6$ experimental group |
| Group D: (65° C., 1 min) LM-LLO540-OVA28 (MOI 0.5)-treated BMDM experimental group |
| five mice in total, each injected with 1 × $10^6$ cells/100 μl, simply referred to as 1 × $10^6$ experimental group (inactivated) |

Cell injection was conducted on Day 10 in PBS control group, BMDM control group, 1×$10^6$ experimental group and 1×$10^6$ experimental group (inactivated), and the tumor sizes were tracked and measured continuously. Tumor sizes were tracked and measured for 19 days.

Figure 14:
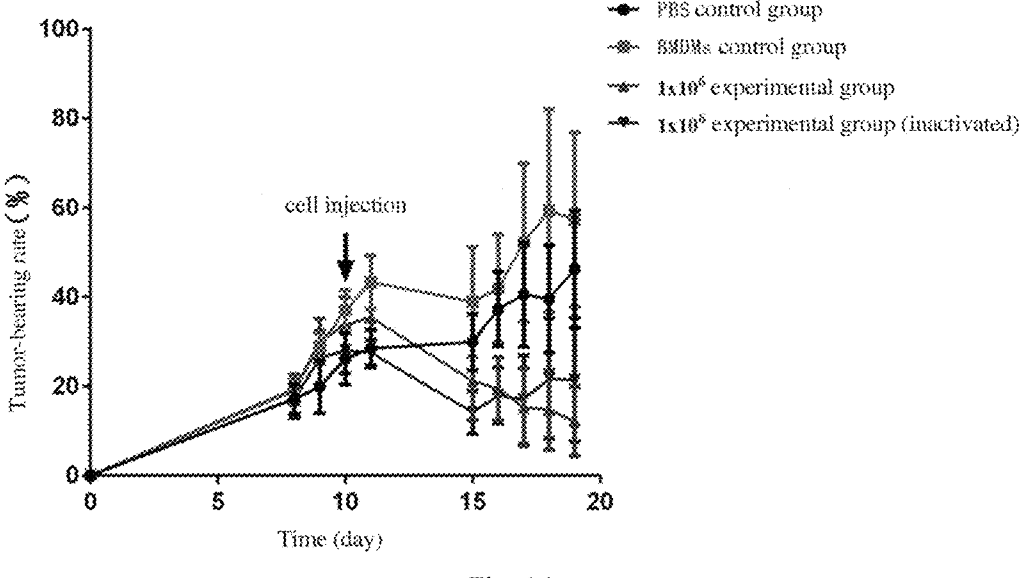
FIG. 14 shows the schematic diagram of the tumor growth curve of EG7 tumor model after the cell therapy.
Figure 15:
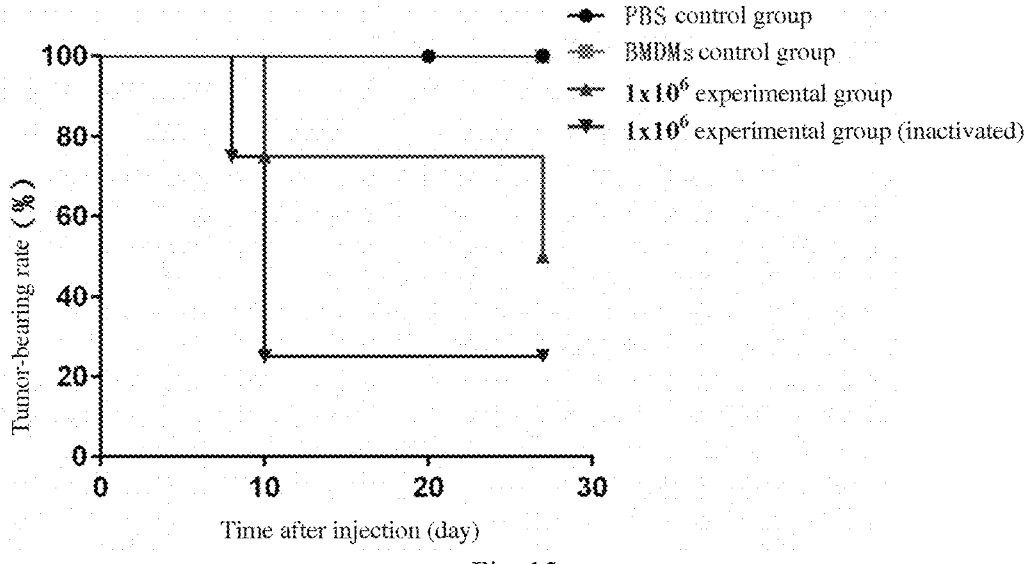
FIG. 15 shows the ladder diagram of the tumor-bearing rate among EG7 tumor models after the cell therapy.

The experimental results were as shown in FIG. 14 and FIG. 15. Among them, tumor growth curve was as shown in FIG. 14. It could be seen that, in 1×10$^6$ experimental group and 1×10$^6$ experimental group (inactivated), a tendency of decrease in tumor size appeared successively from Day 12, and the tumor sizes were reduced to the minimum size till Day 19.

The statistical ladder diagram of the tumor-bearing rates among mice in each group was as shown in FIG. 15, which indicated that the tumor-bearing rates in 1×10$^6$ experimental group and 1×10$^6$ experimental group (inactivated) were lower than that in control group. Such results indicated that using BMDMs treated with an attenuated *Listeria* (inactivated) was also capable of eliciting antitumor response, which greatly enhanced the safety of the use of the attenuated *Listeria*.

Example 18: Verification of the Activation of Tumor-Specific Immune Response by Cell Therapy in EG7 Tumor-Bearing Mouse Model Via ELISPOT Assay ELISPOT assay was conducted for the verification. 3 to 7 drops of blood was drawn via tail vein on Day 7 after the cell injection in cell therapy and washed twice with PBS to obtain peripheral blood mononuclear cells, which were finally re-suspended in 100 μl of 1640 complete culture medium respectively and then added to a pretreated ELISPOT well plate. Subsequently, 10 ng/μl of OVA polypeptide was added to the ELISPOT well plate to stimulate the peripheral blood mononuclear cells to produce IFN-γ. Finally, the number of spots was quantified by enzyme-linked reaction to indicate the specific immune response to OVA polypeptide in each group (for specific protocol of ELISPOT assay, please refer to the specification of BD™ ELISPOT Mouse IFN-γ ELISPOT Set, product number: 551083).

Figure 16:
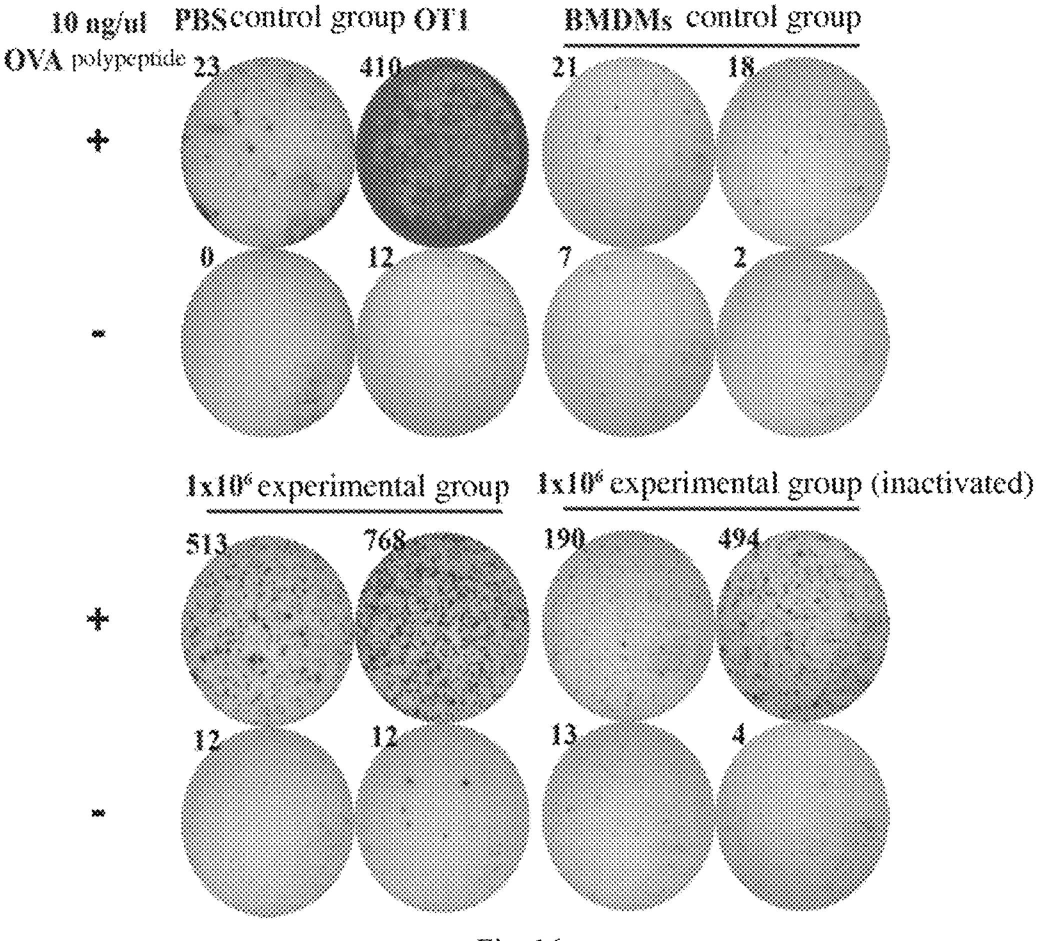
FIG. 16 shows the schematic diagram of the results of ELISPOT response 7 days after the cell therapy.

The experimental results were as shown in FIG. 16. There appeared relatively strong ELISPOT response in both 1×10$^6$ experimental group and 1×10$^6$ experimental group (inactivated), which indicated that BMDMs treated with an attenuated *Listeria* (inactivated) were still capable of activating OVA-specific immune response of the mouse immune system after cell injection, thereby proving the safety and effectiveness of the cell therapy of the present method.

Example 19: Culture of Primary BMDCs 8-week-old female C57 mice were sacrificed by $CO_2$ and cervical dislocation. The femoral neck was incised and placed in 75% alcohol in an ice bath, and transferred into PBS on a clean bench. The muscle layer was isolated with sterilized surgical forceps and surgical scissors, and the femoral neck was transferred to 1640 complete culture medium. The femoral heads at both ends were cut open by a surgical scissor, 1640 complete culture medium was sucked by using a syringe and was used to flush the bone cavity until it became white. The 1640 complete culture medium containing cells were filtered through a mesh, the red blood cells were lysed by red blood cell lysis solution, and cells were collected by centrifugation at 1500 rpm. Cells were re-suspended in 1640 complete culture medium containing 10 ng/μl of GM-CSF and 10 ng/μl of IL4 cytokine. Cells were cultured in an amount enough for each mouse to be inoculated with all the cells cultured on three 10-mm bacterial culture dishes. After two days of differentiation, the liquid cell culture was collected and centrifuged at 3000 rpm, and ice-cold PBS (4° C.) was added to the culture dishes to wash twice. After the centrifugation of the original culture medium, half of the supernatant was taken and added to a culture dish, 5 ml of fresh 1640 complete culture medium containing 10 ng/μl of GM-CSF and 10 ng/μl of IL4 cytokine was taken and added to the culture dish, and the resultant was further incubated in an incubator containing 5% $CO_2$ at 37° C. Afterwards, half of the medium was replaced every two days on Day 4 and Day 6. All the cell culture medium was collected and centrifuged at 1500 rpm, and the supernatant in the upper part was discarded. The precipitated cells were collected, re-suspended and added to a culture dish, in which 5 ml of fresh 1640 complete culture medium containing cytokine was further added. A large amount of bone marrow-derived dendritic cells were harvested on Day 7 or Day 8 and could be used in the experiments.

Example 20: Treating BMDCs with an Attenuated *Listeria* Carrying the Plasmid of a Non-Integrative Antigen Peptide BMDCs cultured up to Day 7 or Day 8 were washed twice with PBS, and 1640 complete culture medium (free of any antibiotics) containing attenuated *Listeria* was added therein. Cells were treated in a cell incubator for 60 min and immediately washed three times with PBS. The culture medium was then replaced with a 1640 complete culture medium containing 5 ng/μl of gentamicin and the extracellular attenuated *Listeria* was treated with the 1640 complete culture medium containing 5 ng/μl of gentamicin for 1 h. The resulting cells could be used in the experiment.

Example 21: Acquisition of C57 Mice Bone Marrow-Derived Dendritic Cells

BMDCs derived from female 8-week-old C57 mice were subjected to primary culture. Red cells in bone marrow cells were lysed and filtered. After centrifugation and cell collection, cells were re-suspended in 1640 complete culture medium containing GM-CSF and IL4-inducing factor and then seeded in 6-well plates for cultivation. Observation was carried out under an inverted phase contrast microscope (40×) on Day 8.

Figure 17:
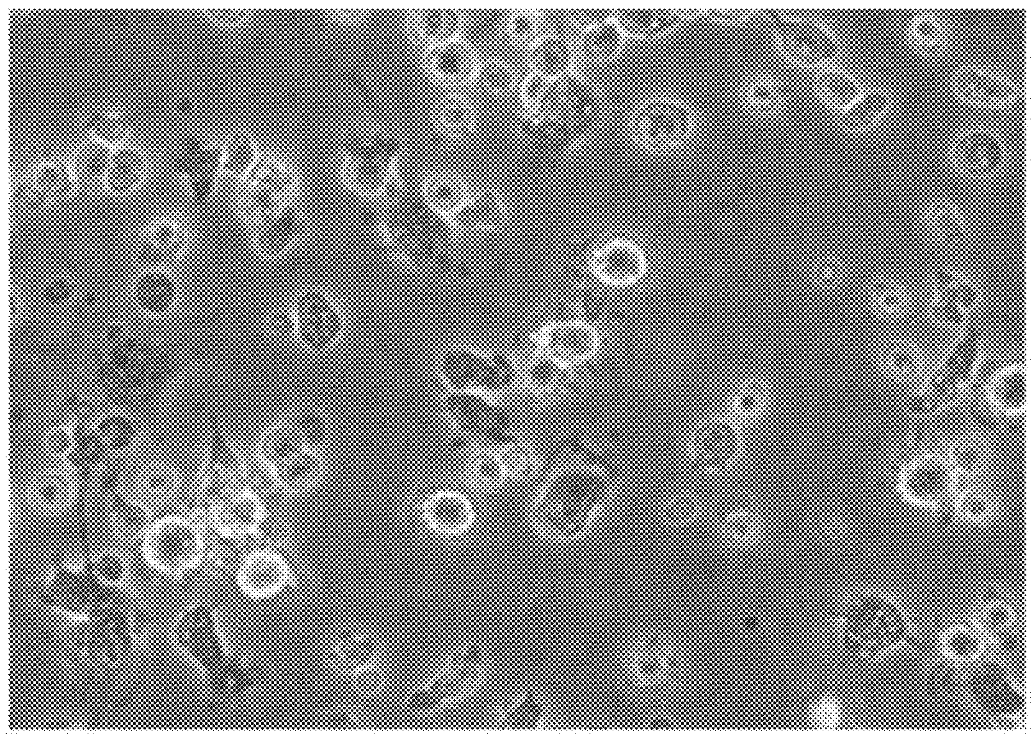
FIG. 17 shows the observation results of the cell morphology of BMDCs on Day 8 of primary culture under an ordinary inverted phase contrast microscope (40×).

The experimental results were as shown in FIG. 17. It was found that some cells were loosely adherent cells, which were attached to the bottom of the culture plate in clusters and clumps and protruded many dendritic pseudopod-like protrusions upon maturation. Such cells were C57 mice bone marrow-derived dendritic cells, which were cultured to Day 7 or Day 8 and then used in the experiment.

Example 22: Inoculating C57 Mice with EG7-OVA Cells, Treating the Mice Via Cell Therapy, and Determining the Antitumor Effects In order to prove the effectiveness of BMDCs in vivo, twenty C57 mice were inoculated subcutaneously with EG7-OVA cells to develop tumors and then treated via cell therapy, and the antitumor effects were determined. The inoculation amount of EG7-OVA cells was 2×10$^6$ cells, and tumor sizes were measured from the 4th day after inoculation. The tumor sizes of 20 mice were normalized and these mice were divided to four groups as below:

| Group A: PBS control group |
|---|
| five mice in total, each injected with 100 μl of PBS via tail vein, simply referred to as PBS control group |
| Group B: LM-LLO540-treated BMDC control group |
| five mice in total, each injected with $1 \times 10^6$ cells/100 μl, simply referred to as BMDC control group |
| Group C: LM-LLO540-OVA28-treated BMDC experimental group |
| five mice in total, each injected with $1 \times 10^6$ cells/100 μl, simply referred to as BMDC experimental group |
| Group D: LM-LLO540-OVA28-treated BMDM experimental group |
| five mice in total, each injected with $1 \times 10^6$ cells/100 μl, simply referred to as BMDM experimental group |

Cell injection was conducted in PBS control group, BMDC control group, BMDC experimental group and BMDM experimental group on Day 11, and tumor sizes were continuously observed. Tumor sizes were tracked and measured until Day 29.

Figure 18:
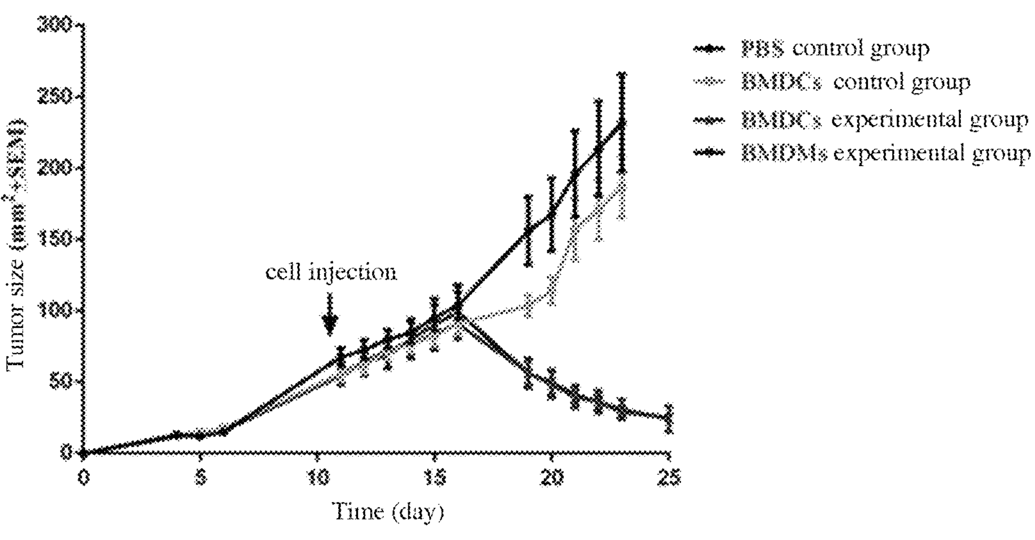
FIG. 18 shows the schematic diagram of the tumor size curve of EG7 tumor model after the cell therapy.
Figure 19:
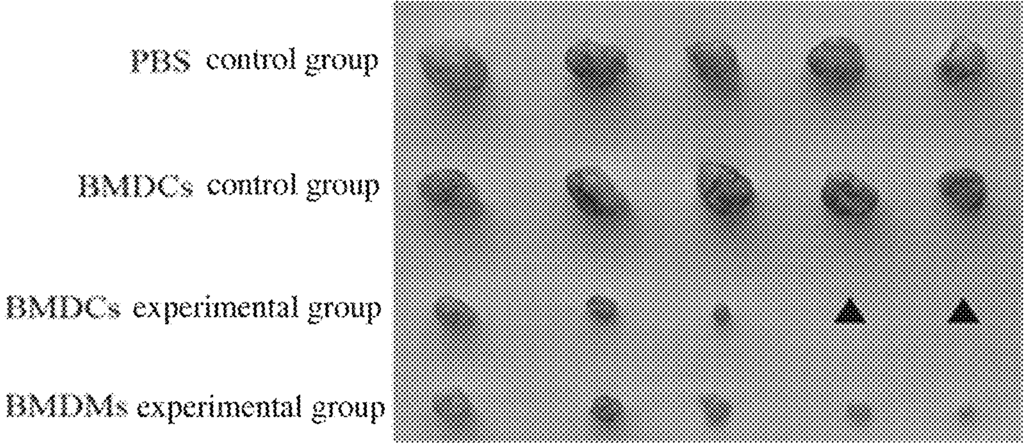
FIG. 19 shows the photograph illustrating the size of the tumors incised from EG7 tumor models after the cell therapy (Δ indicates that the tumor in this tumor-bearing mouse has been completely eliminated).

The experimental results were as shown in FIG. 18 and FIG. 19. Among them, tumor growth curve was as shown in FIG. 18. The tumor sizes in PBS control group and BMDC control group increased with time while the therapeutic effects achieved in BMDC experimental group and BMDM experimental group were basically the same, that is, a tendency of decrease in tumor size appeared from Day 16 and the tumor sizes kept decreasing with time.

Mice were euthanized and the tumors were incised on Day 30, and the tumor sizes conformed to those in the measured growth curve (see FIG. 19). Among them, two individuals in BMDC experimental group showed complete elimination of tumor cells.

Example 23: Verification of the Activation of Tumor-Specific Immune Response by Cell Therapy in EG7 Tumor-Bearing Mouse Model Via ELISPOT Assay In order to further functionally determine the activation of in-vivo tumor-specific immune response in EG7 tumor-bearing mouse model by the cell therapy of the present method, Elispot assay was conducted for verification. 3 to 7 drops of blood was drawn via tail vein on Day 7 after the cell injection in cell therapy, red blood cells were lysed, and the resultant was washed twice with PBS to obtain peripheral blood mononuclear cells, which were finally re-suspended in 100 μl of 1640 complete culture medium respectively and then added to a pretreated Elispot well plate. Subsequently, 10 ng/μl of OVA polypeptide was added to the Elispot well plate to stimulate the peripheral blood mononuclear cells to produce IFN-γ. Finally, the number of spots was quantified by enzyme-linked reaction to indicate the specific immune response to OVA polypeptide in each group (for specific protocol of ELISPOT assay, please refer to the specification of BD™ ELISPOT Mouse IFN-γ ELISPOT Set, product number: 551083).

Figure 20:
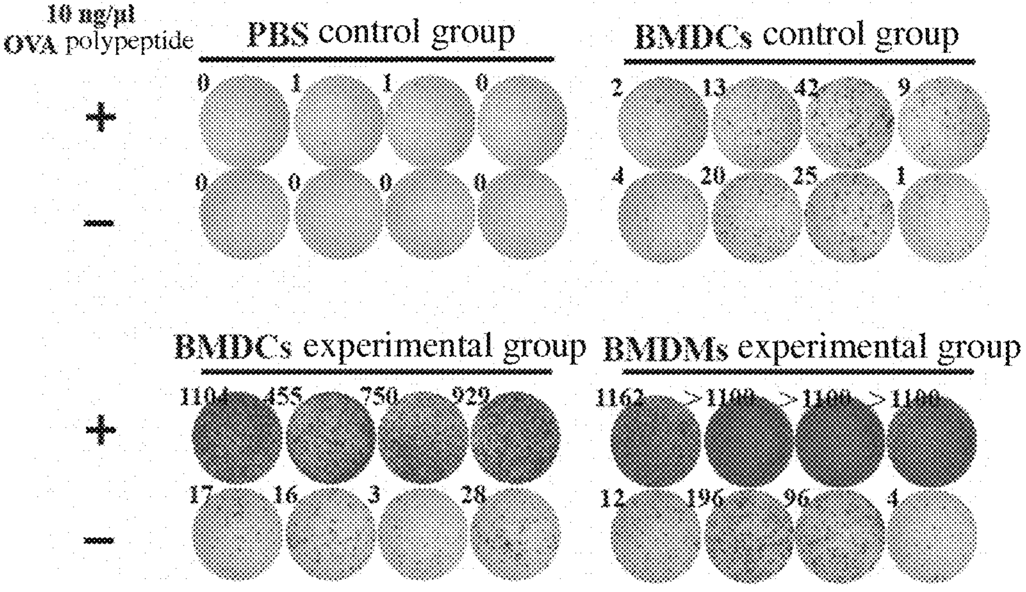
FIG. 20 shows the schematic diagram of the results of ELISPOT response 7 days after the cell therapy.

The experimental results were as shown in FIG. 20. There was no Elispot spot or few Elispot spots in the control group while there was significantly stronger Elispot response in both BMDC experimental group and BMDM experimental group, which indicated that OVA-specific immune response of the mouse immune system could be activated after the cell injection, thereby proving the effectiveness of the cell therapy of the present method.

Example 24: Effectiveness of Different Doses of BMDCs in Tumor Model

In order to further prove the effectiveness of different doses of BMDCs in vivo, twenty-two C57 mice were subcutaneously inoculated with EG7-OVA cells to develop tumors and then treated via cell therapy, and the antitumor effects were verified. The inoculation amount of EG7-OVA cells was $2\times10^6$ cells, and tumor sizes were measured from the 6th day after inoculation. 22 mice were divided into four groups as below according to tumor sizes.

| Group A: PBS control group |
|---|
| 4 mice in total, each injected with 100 μl of PBS via tail vein, simply referred to as PBS control group |
| Group B: LM-LLO540-OVA28-treated BMDC experimental group |
| 6 mice in total, each injected with $1 \times 10^6$ cells/100 μl via tail vein, simply referred to as $1 \times 10^6$ group |
| Group C: LM-LLO540-OVA28-treated BMDC experimental group |
| 6 mice in total, each injected with $1 \times 10^5$ cells/100 μl via tail vein, simply referred to as $1 \times 10^5$ group |
| Group D: LM-LLO540-OVA28-treated BMDC experimental group |
| 6 mice in total, each injected with $1 \times 10^4$ cells/100 μl via tail vein, simply referred to as $1 \times 10^4$ group |

Cell injection was conducted in PBS control group and LM-LLO540-OVA28-treated BMDC experimental groups (i.e., $10^6$, $10^5$, $10^4$ experimental groups) on Day 9. Tumor sizes were tracked and measured continuously until Day 28.

Figure 21:
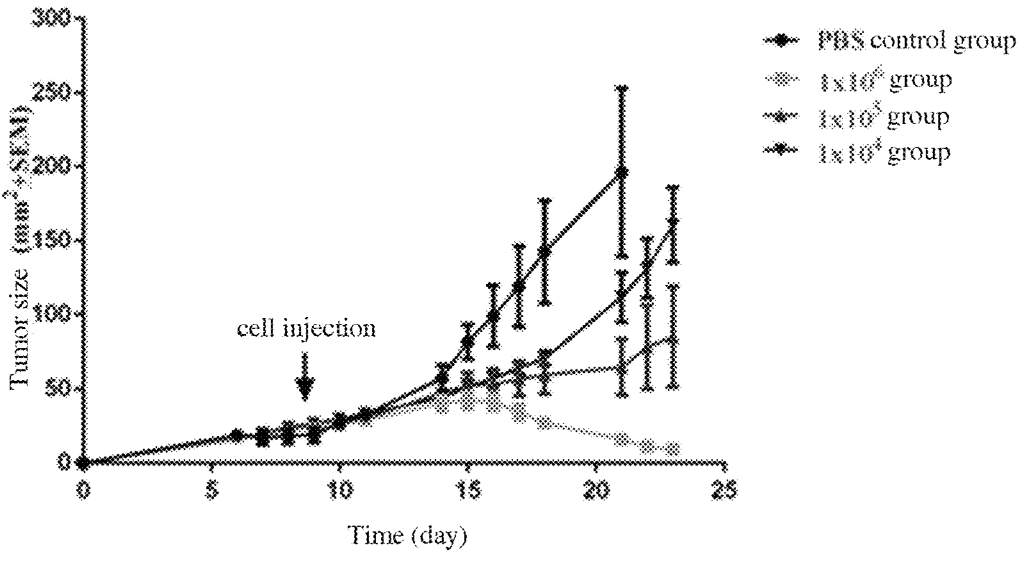
FIG. 21 shows the schematic diagram of the tumor growth curve of EG7 tumor model after the cell therapy.
Figure 22:
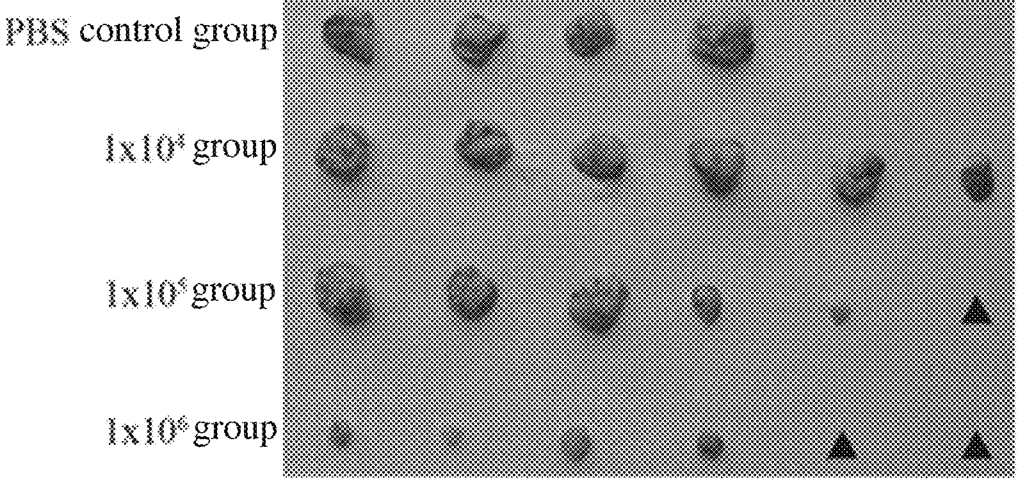
FIG. 22 shows the photograph illustrating the size of the tumors incised from EG7 tumor models after the cell therapy (Δ indicates that the tumor in this tumor-bearing mouse has been completely eliminated).

The tumor growth curve in the experimental results was as shown in FIG. 21. The tumor sizes of the mice in PBS control group and $10^4$ group kept increasing, the tumor growth in mice in $10^5$ group was relatively slow after Day 15, and a tendency of decrease in tumor size appeared after Day 15 in $10^6$ experimental group. The mice were euthanized on Day 23 and the incised tumors were as shown in FIG. 22. The tumors of all mice in $10^6$ group were reduced in size, half of the experimental mice in $10^5$ group showed obvious tumor elimination, and the mice in $10^4$ experimental group showed no sign of tumor elimination, which conformed to the tumor growth curve.

Example 25: Verification of the Activation of Tumor-Specific Immune Response by Cell Therapy in EG7 Tumor-Bearing Mouse Model Via ELISPOT Assay Elispot assay was conducted for verification. 3 to 7 drops of blood was drawn via tail vein on Day 7 after the cell injection in cell therapy, red blood cells were lysed, and the resultant was washed twice with PBS to obtain peripheral blood mononuclear cells, which were finally re-suspended in 100 μl of 1640 complete culture medium respectively and then added to a pretreated Elispot well plate. Subsequently, 10 ng/μl of OVA polypeptide was added to the Elispot well plate to stimulate the peripheral blood mononuclear cells to produce IFN-γ. Finally, the number of spots was quantified by enzyme-linked reaction to indicate the specific immune response to OVA polypeptide in each group (for specific protocol of ELISPOT assay, please refer to the specification of BD™ ELISPOT Mouse IFN-γ ELISPOT Set, product number: 551083).

Figure 23:
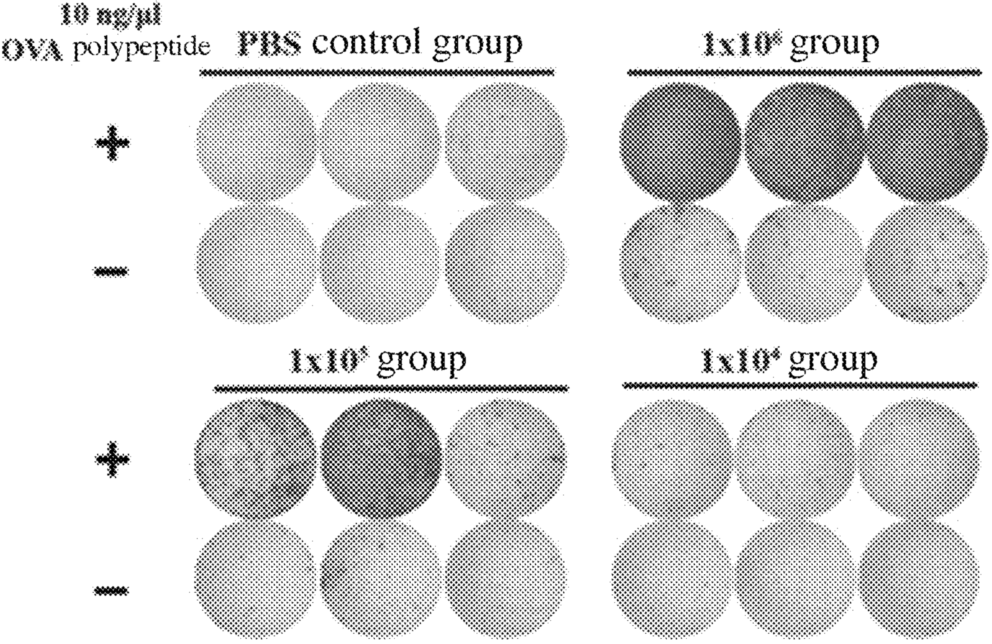
FIG. 23 shows the schematic diagram of the results of ELISPOT response 7 days after the cell therapy.

The experimental results were as shown in FIG. 23. There was no Elispot spot or few Elispot spots in PBS control group and LM-LLO540-OVA28-treated BMDC group ($10^4$ group) while there was significant stronger Elispot response in some of the plates in $10^5$ experimental group and there was significant stronger Elispot response in all plates in $10^6$ experimental group, which indicated that an injection dose of $10^5$ cells to $10^6$ cells was capable of activating OVA-specific immune response of the mouse immune system, thereby further proving the effectiveness of the cell therapy of the present method.

The above-mentioned Examples of the present disclosure are merely exemplified to clearly illustrate the present disclosure rather than limitations to the embodiments of the present disclosure. For those of ordinary skill in the art, other changes or modifications in different forms may also be made based on the foregoing description. It is not necessary and impossible to enumerate all the embodiments. Any modification, equivalent replacement and improvement made within the spirits and principles of this disclosure shall be encompassed in the protection scope of the claims of the present disclosure.

What is claimed is:

1. A population of antigen-presenting cells obtained by contacting said antigen-presenting cells with a recombinant *Listeria* that is attenuated, wherein said recombinant *Listeria* comprises: (i) a recombinant nucleic acid molecule, (ii) a recombinant plasmid, or (iii) a recombinant expression vector; wherein said recombinant *Listeria* expresses (iv) a recombinant protein; wherein said (i) recombinant nucleic acid molecule comprises an open reading frame encoding a recombinant polypeptide, said recombinant polypeptide comprises a heterologous antigen fused to a derived Listeriolysin O (LLO) polypeptide, said recombinant nucleic acid molecule further comprises a first promoter; wherein the amino acid sequence of said derived Listeriolysin O (LLO) polypeptide comprises a first polypeptide sequence of amino acids 1-28 of SEQ ID NO: 2, a second polypeptide sequence of amino acids 22-523 of SEQ ID NO: 2, and a third polypeptide sequence of amino acids 524-529 of SEQ ID NO: 2; wherein said heterologous antigen or a fragment thereof is presented on the surface of at least one of the antigen-presenting cells; said (ii) recombinant plasmid or said (iii) recombinant expression vector comprises the sequence of said (i) recombinant nucleic acid molecule; and said (iv) recombinant protein is encoded by said (i) recombinant nucleic acid molecule, or is expressed by said (ii) recombinant plasmid or said (iii) recombinant expression vector.

2. The antigen-presenting cells of claim 1, wherein the antigen-presenting cells comprise macrophages or dendritic cells.

3. The antigen-presenting cells of claim 2, wherein the antigen-presenting cells comprise macrophages.

4. The antigen-presenting cell of claim 2, wherein the antigen-presenting cells comprise dendritic cells.

5. The antigen-presenting cells of claim 1, wherein said derived Listeriolysin O (LLO) polypeptide comprises an amino acid sequence that is at least 80% identical to SEQ ID NO: 2.

6. The antigen-presenting cells of claim 1, wherein said heterologous antigen is ovalbumin (OVA) or a fragment thereof that comprises an amino acid sequence as set forth in SEQ ID NO: 7.

7. The antigen-presenting cells of claim 1, wherein said (i) recombinant nucleic acid molecule further comprises a linking sequence, wherein said linking sequence links a nucleotide sequence encoding said derived Listeriolysin O (LLO) polypeptide and a nucleotide sequence encoding said heterologous antigen.

8. The antigen-presenting cells of claim 7, wherein said (i) recombinant nucleic acid molecule comprises a nucleotide sequence that is connected to said nucleotide sequence encoding said derived Listeriolysin O (LLO) polypeptide, wherein said nucleotide sequence comprises said linking sequence and said nucleotide sequence encoding said heterologous antigen, wherein said nucleotide sequence encodes an amino acid sequence that is as set forth in SEQ ID NO: 11.

9. The antigen-presenting cells of claim 7, wherein in said (i) recombinant nucleic acid molecule, said linking sequence comprises a nucleotide sequence encoding an amino acid sequence as set forth in SEQ ID NO: 10.

10. The antigen-presenting cells of claim 1, wherein in said (i) recombinant nucleic acid molecule, said first promoter is a Phly promoter.

11. The antigen-presenting cells of claim 10, wherein said recombinant nucleic acid molecule further comprises a tag sequence for detection or a gene encoding a metabolite.

12. A pharmaceutical composition comprising a therapeutically effective amount of the antigen-presenting cells of claim 1, wherein said pharmaceutical composition further comprises a second therapeutic agent or a pharmaceutically acceptable carrier.

13. The antigen-presenting cells of claim 1, wherein the heterologous antigen is a tumor antigen.

14. The antigen-presenting cells of claim 1, wherein the heterologous antigen is a non-tumor antigen.

15. The antigen-presenting cells of claim 1, wherein the open reading frame encoding the recombinant polypeptide comprises a sequence encoding the heterologous antigen inserted between the sequence encoding the first polypeptide sequence and the sequence encoding the second polypeptide sequence.

16. The antigen-presenting cells of claim 1, wherein the open reading frame encoding the recombinant polypeptide comprises a sequence encoding the heterologous antigen inserted between the sequence encoding the second polypeptide sequence and the sequence encoding the third polypeptide sequence.

17. The antigen-presenting cells of claim 1, wherein said recombinant *Listeria* is a recombinant *Listeria L monocytogenes*.

18. A method for slowly and continuously killing cells, comprising contacting said cells with the antigen-presenting cells of claim 1.

19. A method for inducing an immune response in a subject, wherein said method comprises (a) contacting a population of antigen-presenting cells with a recombinant *Listeria* that is attenuated, wherein said recombinant *Listeria* comprises: (i) a recombinant nucleic acid molecule, (ii) a recombinant plasmid, or (iii) a recombinant expression vector; wherein said recombinant *Listeria* expresses (iv) a recombinant protein; wherein said (i) recombinant nucleic acid molecule comprises an open reading frame encoding a recombinant polypeptide, said recombinant polypeptide comprises a heterologous antigen fused to a derived Listeriolysin O (LLO) polypeptide, said recombinant nucleic acid molecule further comprises a first promoter; wherein the amino acid sequence of said derived Listeriolysin O (LLO) polypeptide comprises a first polypeptide sequence of amino acids 1-28 of SEQ ID NO: 2, a second polypeptide sequence of amino acids 22-523 of SEQ ID NO: 2, and a third polypeptide sequence of amino acids 524-529 of SEQ ID NO: 2; wherein said heterologous antigen or a fragment thereof is presented on the surface of at least one of the antigen-presenting cells when the contacting step is finished;

said (ii) recombinant plasmid or said (iii) recombinant expression vector comprises the sequence of said (i) recombinant nucleic acid molecule;

said (iv) recombinant protein is encoded by said (i) recombinant nucleic acid molecule, or is expressed by said (ii) recombinant plasmid or said (iii) recombinant expression vector; and (b) administering said antigen-presenting cells obtained in step (a) to the subject.

20. A method for activating a population of antigen-presenting cells, wherein said method comprises contacting the antigen-presenting cells with a recombinant *Listeria* that is attenuated, wherein said recombinant *Listeria* comprises: (i) a recombinant nucleic acid molecule, (ii) a recombinant plasmid, or (iii) a recombinant expression vector; wherein said recombinant *Listeria* expresses (iv) a recombinant protein; wherein said (i) recombinant nucleic acid molecule comprises an open reading frame encoding a recombinant polypeptide, said recombinant polypeptide comprises a heterologous antigen fused to a derived Listeriolysin O (LLO) polypeptide, said recombinant nucleic acid molecule further comprises a first promoter; wherein the amino acid sequence of said derived Listeriolysin O (LLO) polypeptide comprises a first polypeptide sequence of amino acids 1-28 of SEQ ID NO: 2, a second polypeptide sequence of amino acids 22-523 of SEQ ID NO: 2, and a third polypeptide sequence of amino acids 524-529 of SEQ ID NO: 2; wherein said heterologous antigen or a fragment thereof is presented on the surface of at least one of the antigen-presenting cells when the contacting step is finished;

said (ii) recombinant plasmid or said (iii) recombinant expression vector comprises the sequence of said (i) recombinant nucleic acid molecule;

said (iv) recombinant protein is encoded by said (i) recombinant nucleic acid molecule, or is expressed by said (ii) recombinant plasmid or said (iii) recombinant expression vector;

wherein said contacting occurs in vitro; wherein the antigen-presenting cells comprise macrophages or dendritic cells.

* * * * *

SEQUENCE LISTING

```
<160> NUMBER OF SEQ ID NOS: 11

<210> SEQ ID NO 1
<211> LENGTH: 1587
<212> TYPE: DNA
<213> ORGANISM: Listeria monocytogenes

<400> SEQUENCE: 1

atgaaaaaaa taatgctagt ttttattaca cttatattag ttagtctacc aattgcgcaa      60

caaactgaag caaaggatgc atctgcattc aataaagaaa attcaatttc atccatggca     120

ccaccagcat ctccgcctgc aagtcctaag acgccaatcg aaaagaaaca cgcggatgaa     180

atcgataagt atatacaagg attggattac aataaaaaca atgtattagt ataccacgga     240

gatgcagtga caaatgtgcc gccaagaaaa ggttacaaag atggaaatga atatattgtt     300

gtggagaaaa agaagaaatc catcaatcaa aataatgcag acattcaagt tgtgaatgca     360

atttcgagcc taacctatcc aggtgctctc gtaaaagcga attcggaatt agtagaaaat     420

caaccagatg ttctccctgt aaaacgtgat tcattaacac tcagcattga tttgccaggt     480

atgactaatc aagacaataa aatagttgta aaaaatgcca ctaaatcaaa cgttaacaac     540

gcagtaaata cattagtgga aagatggaat gaaaaatatg ctcaagctta tccaaatgta     600

agtgcaaaaa ttgattatga tgacgaaatg gcttacagtg aatcacaatt aattgcgaaa     660

tttggtacag catttaaagc tgtaaataat agcttgaatg taaacttcgg cgcaatcagt     720

gaagggaaaa tgcaagaaga agtcattagt tttaaacaaa tttactataa cgtgaatgtt     780

aatgaaccta caagaccttc cagatttttc ggcaaagctg ttactaaaga gcagttgcaa     840

gcgcttggag tgaatgcaga aaatcctcct gcatatatct caagtgtggc gtatggccgt     900

caagtttatt tgaaattatc aactaattcc catagtacta aagtaaaagc tgcttttgat     960

gctgccgtaa gcggaaaatc tgtctcaggt gatgtagaac taacaaatat catcaaaaat    1020

tcttccttca aagccgtaat ttacggaggt tccgcaaaag atgaagttca aatcatcgac    1080

ggcaacctcg gagacttacg cgatattttg aaaaaaggcg ctacttttaa tcgagaaaca    1140

ccaggagttc ccattgctta tacaacaaac ttcctaaaag acaatgaatt agctgttatt    1200

aaaaacaact cagaatatat tgaaacaact tcaaaagctt atacagatgg aaaaattaac    1260

atcgatcact ctggaggata cgttgctcaa ttcaacattt cttgggatga agtaaattat    1320

gatcctgaag gtaacgaaat tgttcaacat aaaaactgga gcgaaaacaa taaaagcaag    1380

ctagctcatt tcacatcgtc catctatttg cctggtaacg cgagaaatat taatgtttac    1440
```

```
gctaaagaat gcactggttt agcttgggaa tggtggagaa cggtaattga tgaccggaac   1500

ttaccacttg tgaaaaatag aaatatctcc atctggggca ccacgcttta tccgaaatat   1560

agtaataaag tagataatcc aatcgaa                                       1587


<210> SEQ ID NO 2
<211> LENGTH: 529
<212> TYPE: PRT
<213> ORGANISM: Listeria monocytogenes

<400> SEQUENCE: 2

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350
```

```
Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
        435                 440                 445

Gln His Lys Asn Trp Ser Glu Asn Asn Lys Ser Lys Leu Ala His Phe
    450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
        515                 520                 525

Glu
```

<210> SEQ ID NO 3
<211> LENGTH: 1620
<212> TYPE: DNA
<213> ORGANISM: Listeria monocytogenes

<400> SEQUENCE: 3

```
atgaaaaaaa taatgctagt ttttattaca cttatattag ttagtctacc aattgcgcaa     60

caaactgaag caaaggatgc atcggatcct actgaagcaa aggatgcatc tgcattcaat    120

aaagaaaatt caatttcatc catggcacca ccagcatctc cgcctgcaag tcctaagacg    180

ccaatcgaaa agaaacacgc ggatgaaatc gataagtata tacaaggatt ggattacaat    240

aaaaacaatg tattagtata ccacggagat gcagtgacaa atgtgccgcc aagaaaaggt    300

tacaaagatg gaaatgaata tattgttgtg gagaaaaaga agaaatccat caatcaaaat    360

aatgcagaca ttcaagttgt gaatgcaatt tcgagcctaa cctatccagg tgctctcgta    420

aaagcgaatt cggaattagt agaaaatcaa ccagatgttc tccctgtaaa acgtgattca    480

ttaacactca gcattgattt gccaggtatg actaatcaag acaataaaat cgttgtaaaa    540

aatgccacta aatcaaacgt taacaacgca gtaaatacat tagtggaaag atggaatgaa    600

aaatatgctc aagcttatcc aaatgtaagt gcaaaaattg attatgatga cgaaatggct    660

tacagtgaat cacaattaat tgcgaaattt ggtacagcat ttaaagctgt aaataatagc    720

ttgaatgtaa acttcggcgc aatcagtgaa gggaaaatgc aagaagaagt cattagtttt    780

aaacaaattt actataacgt gaatgttaat gaacctacaa gaccttccag atttttcggc    840

aaagctgtta ctaaagagca gttgcaagcg cttggagtga atgcagaaaa tcctcctgca    900

tatatctcaa gtgtggcgta tggccgtcaa gtttatttga aattatcaac taattcccat    960

agtactaaag taaaagctgc ttttgatgct gccgtaagcg gaaaatctgt ctcaggtgat   1020

gtagaactaa caaatatcat caaaaattct tccttcaaag ccgtaattta cggaggttcc   1080
```

```
gcaaaagatg aagttcaaat catcgacggc aacctcggag acttacgcga tattttgaaa   1140

aaaggcgcta cttttaatcg agaaacacca ggagttccca ttgcttatac aacaaacttc   1200

ctaaaagaca atgaattagc tgttattaaa aacaactcag aatatattga aacaacttca   1260

aaagcttata cagatggaaa aattaacatc gatcactctg gaggatacgt tgctcaattc   1320

aacatttctt gggatgaagt aaattatgat cctgaaggta acgaaattgt tcaacataaa   1380

aactggagcg aaaacaataa aagcaagcta gctcatttca catcgtccat ctatttgcca   1440

ggtaacgcga gaaatattaa tgtttacgct aaagaatgca ctggtttagc ttgggaatgg   1500

tggagaacgg taattgatga ccggaactta ccacttgtga aaaatagaaa tatctccatc   1560

tggggcacca cgctttatcc gaaatatagt aataaactgc aggtagataa tccaatcgaa   1620


<210> SEQ ID NO 4
<211> LENGTH: 540
<212> TYPE: PRT
<213> ORGANISM: Listeria monocytogenes

<400> SEQUENCE: 4

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Asp Pro Thr Glu
            20                  25                  30

Ala Lys Asp Ala Ser Ala Phe Asn Lys Glu Asn Ser Ile Ser Ser Met
        35                  40                  45

Ala Pro Pro Ala Ser Pro Pro Ala Ser Pro Lys Thr Pro Ile Glu Lys
    50                  55                  60

Lys His Ala Asp Glu Ile Asp Lys Tyr Ile Gln Gly Leu Asp Tyr Asn
65                  70                  75                  80

Lys Asn Asn Val Leu Val Tyr His Gly Asp Ala Val Thr Asn Val Pro
                85                  90                  95

Pro Arg Lys Gly Tyr Lys Asp Gly Asn Glu Tyr Ile Val Val Glu Lys
            100                 105                 110

Lys Lys Lys Ser Ile Asn Gln Asn Asn Ala Asp Ile Gln Val Val Asn
        115                 120                 125

Ala Ile Ser Ser Leu Thr Tyr Pro Gly Ala Leu Val Lys Ala Asn Ser
    130                 135                 140

Glu Leu Val Glu Asn Gln Pro Asp Val Leu Pro Val Lys Arg Asp Ser
145                 150                 155                 160

Leu Thr Leu Ser Ile Asp Leu Pro Gly Met Thr Asn Gln Asp Asn Lys
                165                 170                 175

Ile Val Val Lys Asn Ala Thr Lys Ser Asn Val Asn Asn Ala Val Asn
            180                 185                 190

Thr Leu Val Glu Arg Trp Asn Glu Lys Tyr Ala Gln Ala Tyr Pro Asn
        195                 200                 205

Val Ser Ala Lys Ile Asp Tyr Asp Asp Glu Met Ala Tyr Ser Glu Ser
    210                 215                 220

Gln Leu Ile Ala Lys Phe Gly Thr Ala Phe Lys Ala Val Asn Asn Ser
225                 230                 235                 240

Leu Asn Val Asn Phe Gly Ala Ile Ser Glu Gly Lys Met Gln Glu Glu
                245                 250                 255

Val Ile Ser Phe Lys Gln Ile Tyr Tyr Asn Val Asn Val Asn Glu Pro
            260                 265                 270

Thr Arg Pro Ser Arg Phe Phe Gly Lys Ala Val Thr Lys Glu Gln Leu
```

```
        275                 280                 285

Gln Ala Leu Gly Val Asn Ala Glu Asn Pro Pro Ala Tyr Ile Ser Ser
    290                 295                 300

Val Ala Tyr Gly Arg Gln Val Tyr Leu Lys Leu Ser Thr Asn Ser His
305                 310                 315                 320

Ser Thr Lys Val Lys Ala Ala Phe Asp Ala Ala Val Ser Gly Lys Ser
                325                 330                 335

Val Ser Gly Asp Val Glu Leu Thr Asn Ile Ile Lys Asn Ser Ser Phe
            340                 345                 350

Lys Ala Val Ile Tyr Gly Gly Ser Ala Lys Asp Glu Val Gln Ile Ile
        355                 360                 365

Asp Gly Asn Leu Gly Asp Leu Arg Asp Ile Leu Lys Lys Gly Ala Thr
    370                 375                 380

Phe Asn Arg Glu Thr Pro Gly Val Pro Ile Ala Tyr Thr Thr Asn Phe
385                 390                 395                 400

Leu Lys Asp Asn Glu Leu Ala Val Ile Lys Asn Asn Ser Glu Tyr Ile
                405                 410                 415

Glu Thr Thr Ser Lys Ala Tyr Thr Asp Gly Lys Ile Asn Ile Asp His
            420                 425                 430

Ser Gly Gly Tyr Val Ala Gln Phe Asn Ile Ser Trp Asp Glu Val Asn
        435                 440                 445

Tyr Asp Pro Glu Gly Asn Glu Ile Val Gln His Lys Asn Trp Ser Glu
    450                 455                 460

Asn Asn Lys Ser Lys Leu Ala His Phe Thr Ser Ser Ile Tyr Leu Pro
465                 470                 475                 480

Gly Asn Ala Arg Asn Ile Asn Val Tyr Ala Lys Glu Cys Thr Gly Leu
                485                 490                 495

Ala Trp Glu Trp Trp Arg Thr Val Ile Asp Asp Arg Asn Leu Pro Leu
            500                 505                 510

Val Lys Asn Arg Asn Ile Ser Ile Trp Gly Thr Thr Leu Tyr Pro Lys
        515                 520                 525

Tyr Ser Asn Lys Leu Gln Val Asp Asn Pro Ile Glu
    530                 535                 540
```

<210> SEQ ID NO 5
<211> LENGTH: 84
<212> TYPE: DNA
<213> ORGANISM: Gallus gallus

<400> SEQUENCE: 5

```
gatgaagtct caggccttga gcagcttgag agtataatca actttgaaaa actgactgaa     60

tggaccagtt ctaatgttat ggaa                                            84
```

<210> SEQ ID NO 6
<211> LENGTH: 84
<212> TYPE: DNA
<213> ORGANISM: Gallus gallus

<400> SEQUENCE: 6

```
gatgaagtga gcggcctgga gcagctggag agcattatca acttcgaaaa actgaccgag     60

tggaccagca gcaatgtgat ggaa                                            84
```

<210> SEQ ID NO 7
<211> LENGTH: 28
<212> TYPE: PRT
<213> ORGANISM: Gallus gallus

```
<400> SEQUENCE: 7

Asp Glu Val Ser Gly Leu Glu Gln Leu Glu Ser Ile Ile Asn Phe Glu
1               5                   10                  15

Lys Leu Thr Glu Trp Thr Ser Ser Asn Val Met Glu
            20                  25


<210> SEQ ID NO 8
<211> LENGTH: 24
<212> TYPE: DNA
<213> ORGANISM: Artificial
<220> FEATURE:
<223> OTHER INFORMATION: synthetic oligonucleotide

<400> SEQUENCE: 8

ccgaaatata gtaataaact gcag                                            24


<210> SEQ ID NO 9
<211> LENGTH: 24
<212> TYPE: DNA
<213> ORGANISM: Artificial
<220> FEATURE:
<223> OTHER INFORMATION: synthetic oligonucleotide

<400> SEQUENCE: 9

ctgcaggtag ataatccaat cgaa                                            24


<210> SEQ ID NO 10
<211> LENGTH: 10
<212> TYPE: PRT
<213> ORGANISM: Artificial
<220> FEATURE:
<223> OTHER INFORMATION: synthetic polypeptide

<400> SEQUENCE: 10

Gly Gly Gly Gly Ser Gly Gly Gly Gly Ser
1               5                   10


<210> SEQ ID NO 11
<211> LENGTH: 48
<212> TYPE: PRT
<213> ORGANISM: Artificial
<220> FEATURE:
<223> OTHER INFORMATION: synthetic polypeptide

<400> SEQUENCE: 11

Gly Gly Gly Gly Ser Gly Gly Gly Gly Ser Asp Glu Val Ser Gly Leu
1               5                   10                  15

Glu Gln Leu Glu Ser Ile Ile Asn Phe Glu Lys Leu Thr Glu Trp Thr
            20                  25                  30

Ser Ser Asn Val Met Glu Gly Gly Gly Gly Ser Gly Gly Gly Gly Ser
        35                  40                  45
```